United States Patent
Briggs et al.

(10) Patent No.: US 6,261,262 B1
(45) Date of Patent: Jul. 17, 2001

(54) PUMP WITH ANTI-FREE FLOW FEATURE

(75) Inventors: Kenneth D. Briggs, San Jose; Allen C. Hall, Palo Alto; Russel M. Sampson, Mountain View, all of CA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 08/873,475

(22) Filed: Jun. 12, 1997

(51) Int. Cl.[7] .............................. A61M 1/00; A61M 5/00; F16K 7/04
(52) U.S. Cl. ............................... 604/153; 604/249; 251/7
(58) Field of Search ................................ 604/153, 30, 34, 604/65, 151, 250, 245, 246, 200, 251; 251/7; 417/474, 480

(56) References Cited

U.S. PATENT DOCUMENTS

| | | |
|---|---|---|
| 4,155,362 | 5/1979 | Jess . |
| 4,397,642 | 8/1983 | Lamadrid . |
| 4,496,351 | 1/1985 | Hillel et al. . |
| 4,565,500 | 1/1986 | Jeensalute et al. . |
| 4,585,441 | 4/1986 | Archibald . |
| 4,586,691 | 5/1986 | Kozlow . |
| 4,689,043 | 8/1987 | Bisha . |
| 4,811,928 | 3/1989 | Iwatschenko et al. . |
| 4,845,487 | 7/1989 | Frantz et al. . |
| 5,017,192 | 5/1991 | Dodge et al. . |
| 5,219,327 | 6/1993 | Okada . |
| 5,257,978 | 11/1993 | Haber et al. . |

(List continued on next page.)

FOREIGN PATENT DOCUMENTS

| | | |
|---|---|---|
| 0423978 | 4/1991 | (EP) . |
| 0447985 | 9/1991 | (EP) . |
| 0483794 | 5/1992 | (EP) . |
| 0510881 | 10/1992 | (EP) . |
| 0569030 | 11/1993 | (EP) . |
| WO9305829 | 4/1993 | (WO) . |
| WO9531233 | 11/1995 | (WO) . |

OTHER PUBLICATIONS

Copy of brochure entitled "imed," published by IMED Corporation, Copyright date 1989.
Photograph labeled "IMED-1".
Copy of brochure entitled "Flo-Gard 6301," published by Baxter Healthcare Corporation, Copyright date 1992.
Photograph labeled "Baxter-1".
Sheet entitled "Breeze™ 175 Volumetric Pump Graphic 2B: Pumping Chamber" illustrating the tubing-receiving region of a LifeCare® 175 Breeze Volumetric Infusion System sold in the U.S.A. by Abbott Laboratories.
Sheet entitled "ASM. Mechanism LC175 (cc) 840–07007, Rev. T" illustrating the tubing-receiving region of a LifeCare® 175 Breeze Volumetric Infusion System sold in the U.S.A. by Abbott Laboratories.
International Search Report, PCT/US98/11915, Sep. 29, 1998.

(List continued on next page.)

Primary Examiner—Richard K. Seidel
Assistant Examiner—Michael A. Hayes
(74) Attorney, Agent, or Firm—Beth A. Vrioni; Brian R. Woodworth

(57) ABSTRACT

A peristaltic pump is provided with a housing, a pump head in the housing, and a receiving path defined along a housing and pump head for receiving tubing. A door is pivotable about an axis between a closed position covering the receiving path and an open position exposing the receiving path. A carrier is provided on the housing for holding an anti-free flow slide clamp on the tubing in the receiving path. The carrier is movable relative to the housing so as to automatically effect closure of the tubing by the slide clamp when the door is opened.

35 Claims, 17 Drawing Sheets

U.S. PATENT DOCUMENTS

| | | |
|---|---|---|
| 5,346,466 | 9/1994 | Yerlikaya et al. . |
| 5,364,364 | 11/1994 | Kasvikis et al. . |
| 5,401,256 | 3/1995 | Stone et al. . |
| 5,437,635 * | 8/1995 | Fields et al. .......................... 604/65 |
| 5,453,098 | 9/1995 | Botts et al. . |
| 5,482,446 | 1/1996 | Williamson et al. . |
| 5,782,805 | 7/1998 | Meinzer et al. . |

OTHER PUBLICATIONS

Operator's Manual, Baxter Flo–Gard 6200, Volumetric Infusion Pump, Copyright 1989.

Operator's Manual, Baxter Flo–Gard 6201. Flo–Gard 6201 sold prior to Jun. 12, 1996.

* cited by examiner

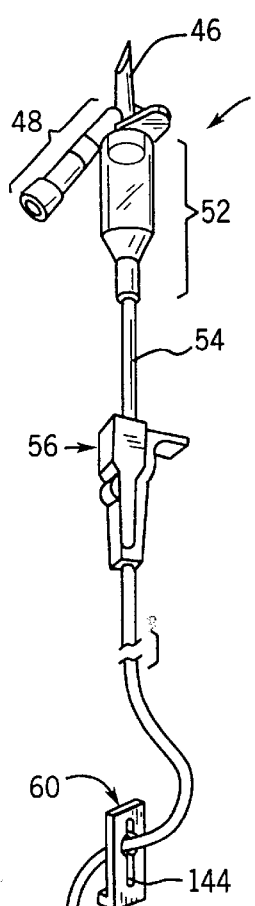
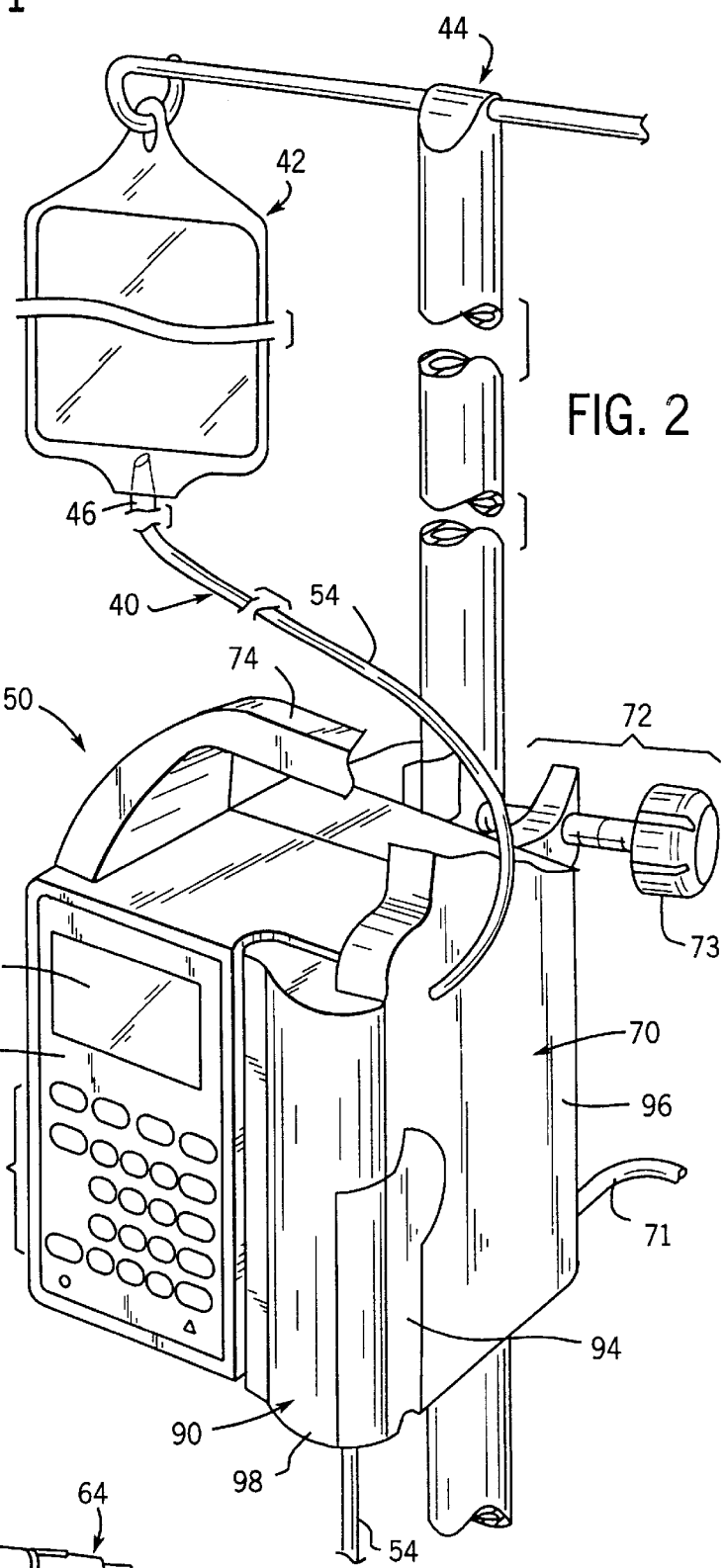
FIG. 1
FIG. 2

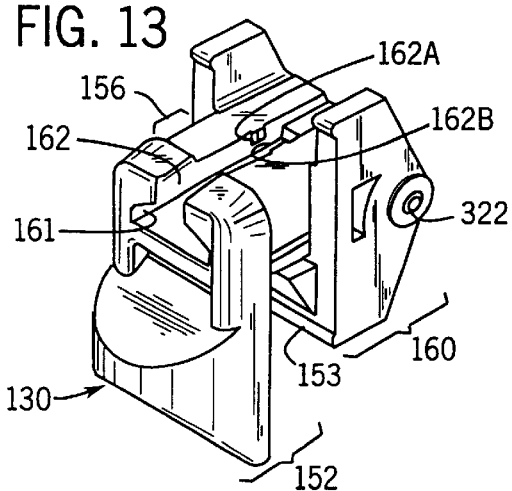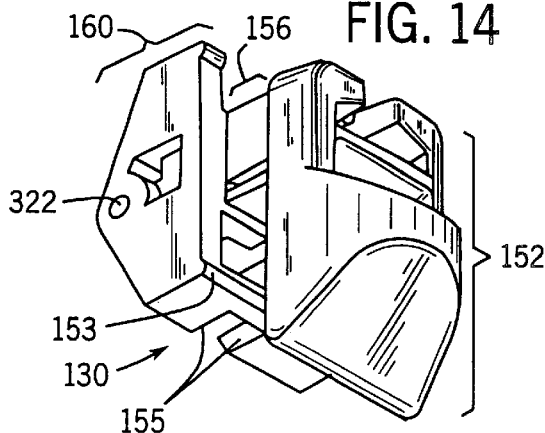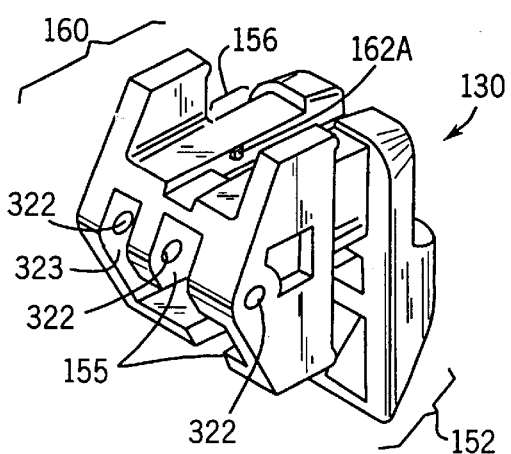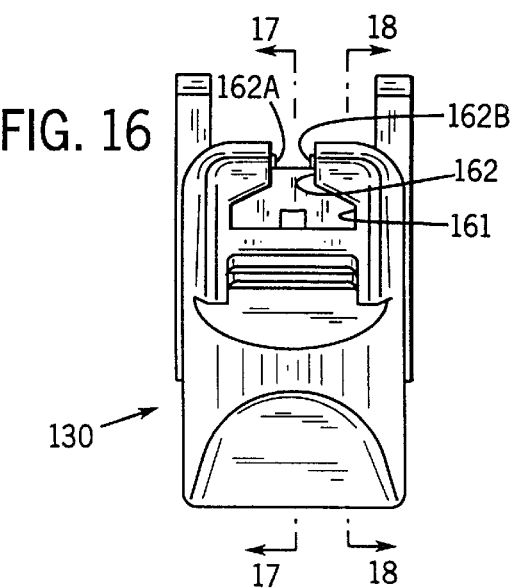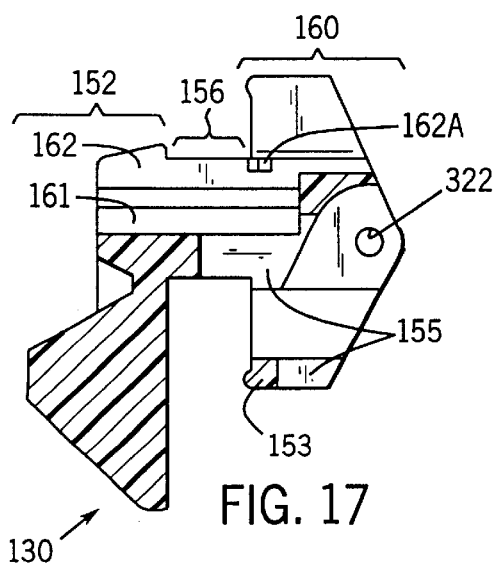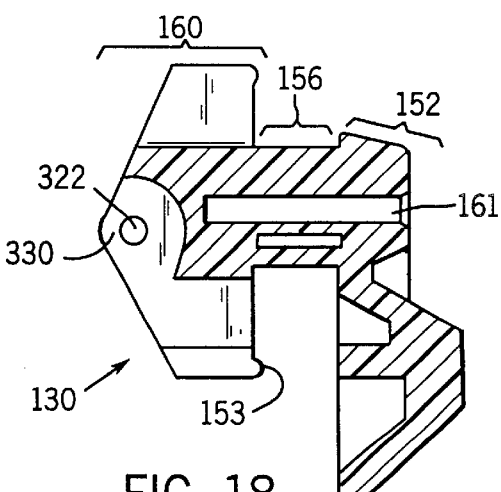

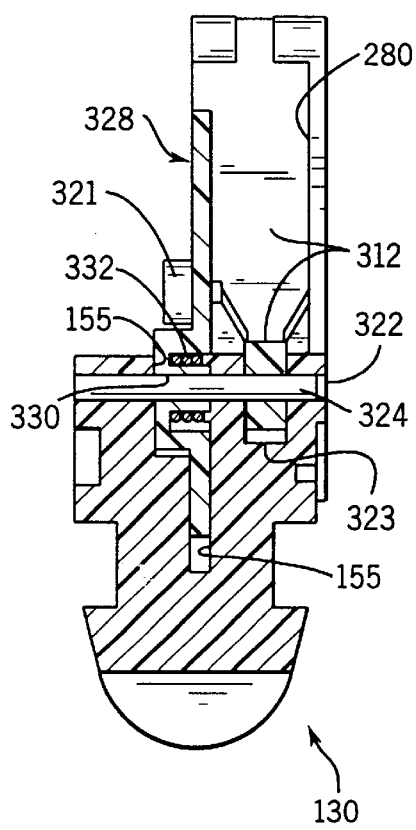
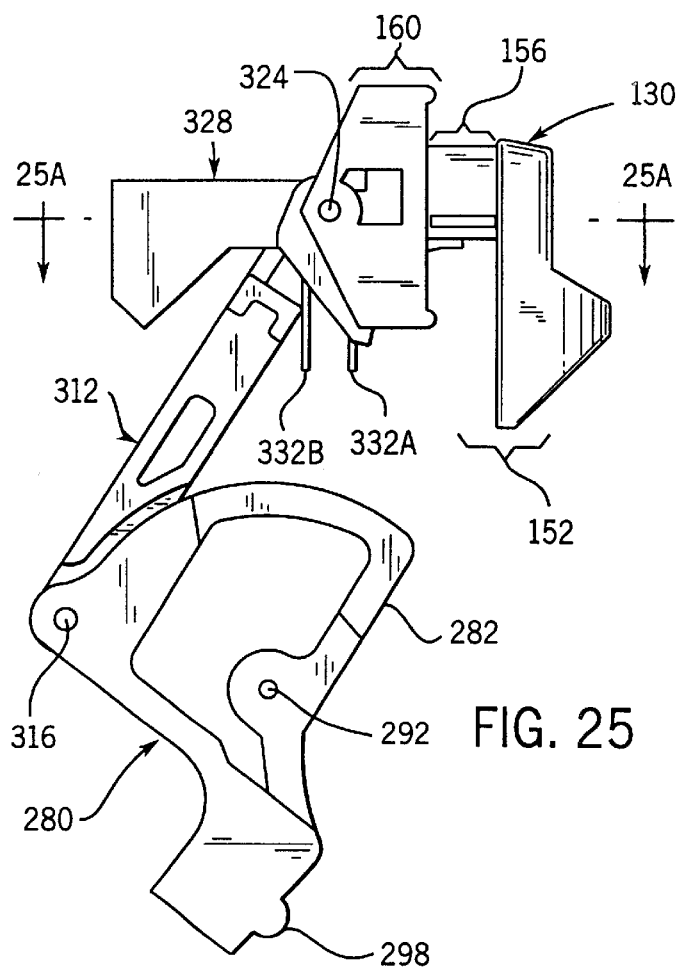
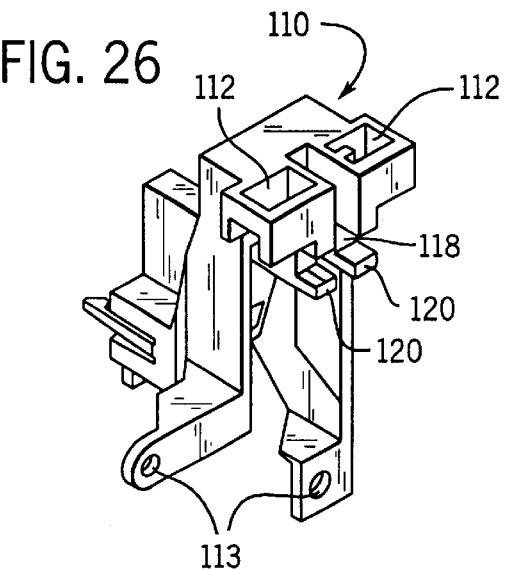
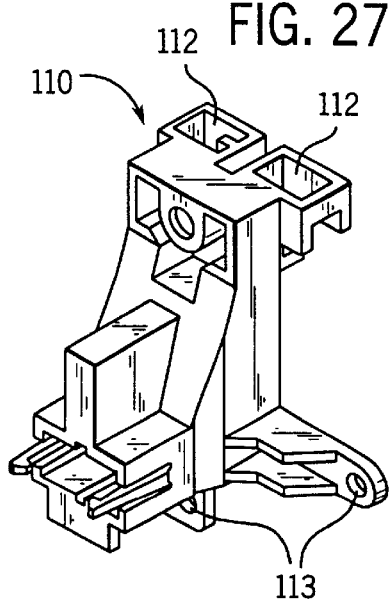

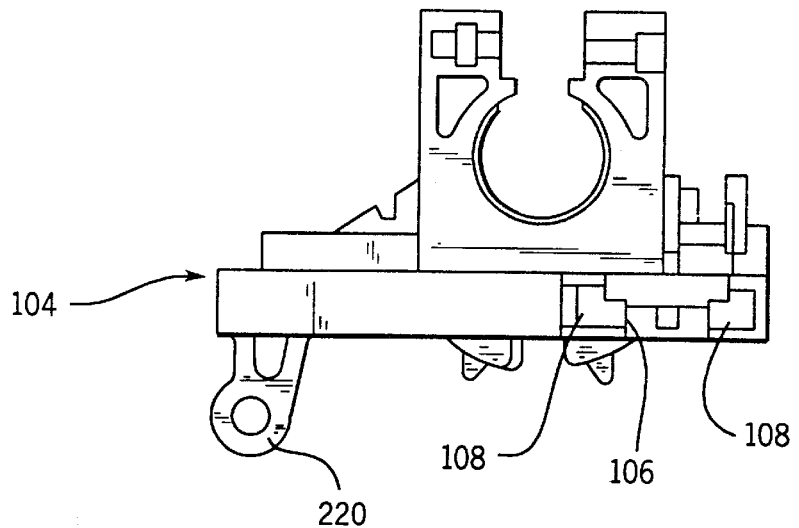
FIG. 30
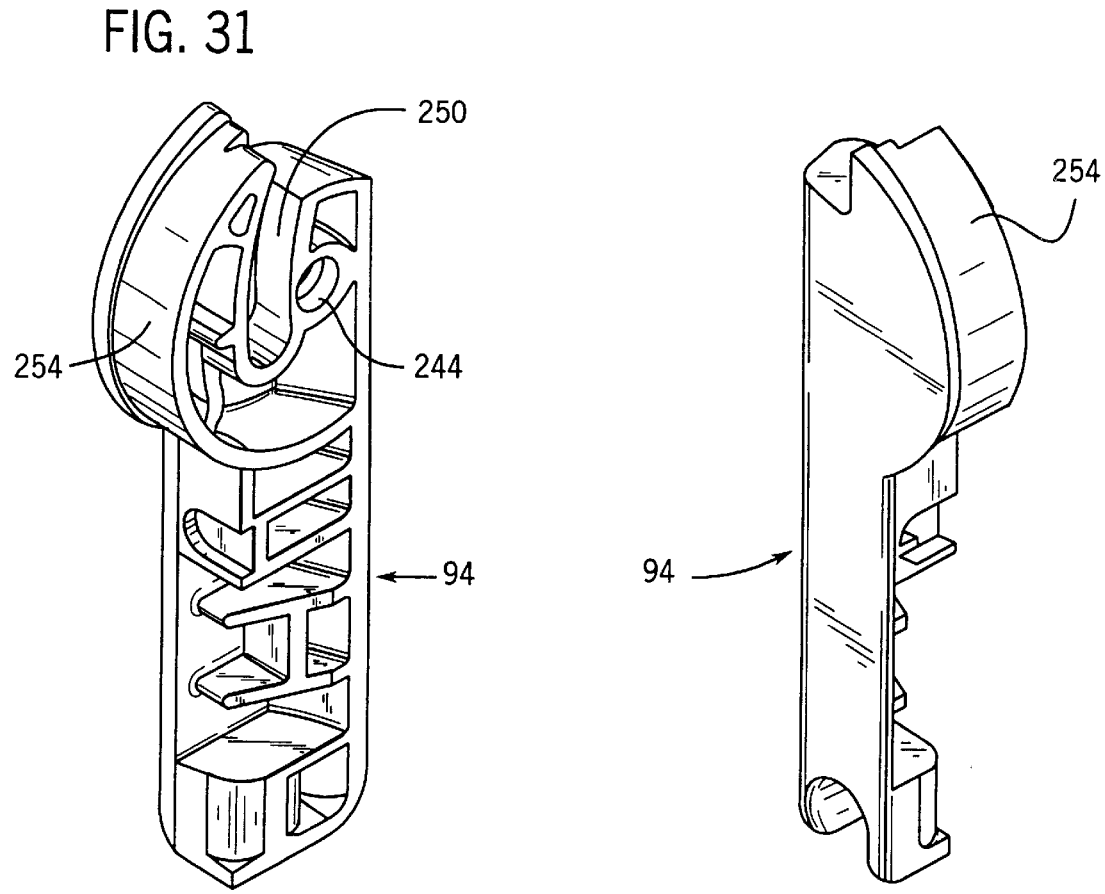
FIG. 31
FIG. 32

PUMP WITH ANTI-FREE FLOW FEATURE

CROSS REFERENCE TO RELATED APPLICATION(S)

Not applicable.

STATEMENT REGARDING FEDERALLY SPONSORED RESEARCH OR DEVELOPMENT

Not applicable.

REFERENCE TO A MICROFICHE APPENDIX

Not applicable.

TECHNICAL FIELD

This invention relates to a liquid delivery system and is especially suitable for use as part of an infusion pump system designed to deliver parenteral and enteral fluids, as well as whole blood or red blood cell components, using a wide variety of standard intravenous administration sets and fluid containers.

BACKGROUND OF THE INVENTION

AND

TECHNICAL PROBLEMS POSED BY THE PRIOR ART

One conventional type of infusion pump system employs a peristaltic pump in conjunction with an intravenous administration set. The set consists of flexible thermoplastic tubing through which fluid flows from a suspended container, such as a flexible bag or rigid bottle, to a patient's indwelling vein access device, such as a needle or cannula inserted into the patient. A length of the administration set tubing between the fluid container and the patient is mounted in the peristaltic pump which sequentially squeezes adjacent sections of the tubing so as to pump the fluid via a peristaltic action along the tubing into the patient.

While such pumping systems function generally satisfactorily, there are some disadvantages with various commercial products employing such systems. For example, when medical personnel remove the tubing from the pump, care must be taken to insure that the tubing has been closed with a suitable device, typically a slide clamp, so as to prevent free flow of the fluid from the container into the patient. Thus, it would be desirable to provide an improved system in which the tubing is automatically closed by a suitable clamp before the tubing is removed from the pump.

Further, it would be beneficial if such an improved system could be employed with a relatively simple clamp mounted on the tubing. Preferably, such an improved system should be capable of functioning with a simple or standard slide clamp on standard intravenous administration set tubing and should not require the use of a more complicated, multi-piece clamping mechanism on such tubing.

Typically, a standard intravenous administration set is disposable and is provided to medical personnel in a sterile, protective package. It would be desirable to provide such an administration set with a tubing clamp that can be automatically operated by the improved pump system and that has a relatively simple design which employs a relatively small size and shape facilitating low cost manufacture, which is easy to sterilize, and which is convenient to package, store, and handle.

Further, an improved infusion pump system should accommodate relatively simple assembly procedures. In particular, it would be desirable to provide an improved infusion pump system wherein the administration set tubing can be loaded into the infusion pump in a logical, and preferably intuitive, manner—starting at the top of the pump and terminating at the bottom of the pump. Such a simple tubing loading process can be easier to learn and is less likely to be improperly executed than less intuitive processes.

The present invention provides an improved infusion pump system which can accommodate designs that have the above-discussed benefits and features, which is convenient to use, and which is cost-effective with respect to its manufacture and operation. The system is easily operated and can be used with a wide variety of standard administration sets and fluid containers. The system is designed to meet the growing demand for hospital-wide standardization, as well as alternatesite, in-home healthcare standardization.

SUMMARY OF THE INVENTION

The improved system of the present invention accommodates safe delivery of fluids to a patient. The system is convenient to operate and is easy to set up.

In the preferred embodiment, the system does not permit the loading of the administration set tubing into the pump with an anti-free flow slide clamp unless the clamp is initially in a fail-safe, closed condition on the tubing.

Further, in the preferred embodiment, the pump includes a door closure system which functions to (1) automatically open the anti-free flow slide clamp when the door is closed, and (2) automatically close the anti-free flow slide clamp when the door is opened. The medical operator of the system need not take any special step upon opening the pump door to ensure that the tubing is closed by at least one clamp. This eliminates, or at least minimizes, the possibility of fluid free flowing into a patient upon removal of the tubing from the pump.

The preferred embodiment of the system also accommodates a variety of standard, gravity, intravenous administration sets. Such sets can be conveniently loaded into the pump in a logical, intuitive, top-to-bottom sequence involving relatively few manual operations.

Further, the improved system can be readily accommodated in an infusion pump having a variety of other conventional or special features relating to automatic pumping operation, air purging, flow occlusion monitoring, air-in-line sensing, alarm features, self-test and diagnostic systems, volume/time programming for automatic secondary flow rate calculations, nurse callback, battery backup, etc.

One aspect of the present invention provides a system for delivering fluid through tubing. The system includes a clamp for clamping the tubing. A pump includes a housing having a receiving path for receiving the tubing through which the fluid is pumped. The pump also includes a carrier mounted in the housing for carrying the clamp on the housing. The carrier is movable relative to the housing, but is not intended to be removable during normal operation of the system.

Another aspect of the present invention relates to an improvement in a pump. The pump includes (1) a receiving path for receiving tubing extending from an inlet end of the path to an outlet end of the path, and (2) a peristaltic pump head along the receiving path between the inlet end and the outlet end. A carrier is provided in the pump adjacent the receiving path between the inlet end and pump head. The carrier is adapted to receive an anti-free flow clamp in a closed condition squeezing the tubing into a closed configuration. A portion of the clamp is positioned by the carrier across the receiving path.

In a preferred embodiment of the invention, the clamp has an open condition in which the tubing is free to return to an open configuration. The tubing, with the clamp disposed thereon, can be loaded into the receiving path of the pump from the inlet end to the outlet end.

According to another aspect of the invention, a peristaltic pump includes a housing which defines (1) a receiving path for receiving tubing extending from an inlet end of the path to an outlet end of the path, and (2) a groove that is (a) oriented generally normal to a portion of the receiving path, and (b) communicates with the receiving path. Mounted in the pump is a carrier into which can be inserted an anti free-flow clamp. In the preferred embodiment, the clamp is inserted in a closed condition squeezing the tubing into a closed configuration. The carrier is located adjacent the housing receiving path and groove. The carrier defines first and second slots for receiving portions of the clamp. The second slot extends from the first slot, and the second slot is generally normal to the first slot and is aligned with the housing groove.

According to yet another aspect of the invention, a pump includes a housing having a receiving path for receiving tubing through which fluid is pumped. The pump has a door pivotal about an axis. In the preferred embodiment, the door can be pivoted between a closed position covering the receiving path and an open position exposing the receiving path. A carrier means is provided on the housing for carrying a clamp on the tubing. The carrier means is movable relative to the housing in a direction parallel to the door axis.

According to yet a further aspect of the invention, a pump includes a housing, a receiving path defined along the housing for receiving tubing, and a door pivotal about an axis between a closed position covering the receiving path and an open position exposing the receiving path. The pump includes a carrier on the housing for holding an anti-free flow slide clamp. The carrier is adapted to hold the clamp in an orientation wherein the clamp aperture lies in a plane parallel to the door axis. In the preferred embodiment, the clamp defines an elongate aperture having (1) a narrow portion for squeezing the tubing into a closed configuration, and (2) a wide portion for receiving the tubing in an unsqueezed, open configuration.

Yet another aspect of the present invention includes a pump which has a housing. A receiving path is defined along the housing for receiving tubing. A carrier is provided on the housing for holding an anti-free-flow slide clamp. The carrier is movable relative to the housing. In the preferred embodiment, the receiving path is defined substantially in a plane along the housing, and the carrier is movable in a direction parallel to the plane defined by the receiving path.

According to another aspect of the invention, a pump is provided with a housing having a receiving path that includes at least a portion lying in a straight line and that is adapted to receive tubing through which fluid is pumped. The pump further includes a carrier means on the housing for carrying a clamp on the tubing. The carrier means is movable relative to said housing in a direction parallel to the straight line portion of the receiving path.

Numerous other advantages and features of the present invention will become readily apparent from the following detailed description of the invention, from the claims, and from the accompanying drawings.

BRIEF DESCRIPTION OF THE DRAWINGS

In the accompanying drawings that form part of the specification, and in which like numerals are employed to designate like parts throughout the same, FIG. 1 is a perspective view of a primary, intravenous administration set;

FIG. 2 is a fragmentary, perspective view of an infusion pump that (1) incorporates features of the present invention, and (2) is mounted on an infusion stand supporting a flexible bag container connected to the administration set which is shown in FIG. 1 and which is illustrated in FIG. 2 as loaded in the infusion pump;

FIG. 3 shows the door in the full open position and the administration set tubing removed from the pump;

FIG. 4 illustrates the administration set tubing-receiving path portion of the pump;

FIG. 7A shows the slide clamp inserted into the pump in a closed condition on the tubing so as to squeeze the tubing closed;

FIG. 10 is taken along the plane 10—10 in FIG. 9 below the upper part of the housing;

FIG. 13 is a front, perspective view of the carrier for the administration tubing set slide clamp, and the carrier is shown removed from the pump in an orientation as it would appear if it were in the pump and viewed from the front, upper, right-hand corner of the pump;

FIG. 14 is a perspective view of the carrier as viewed from the front, lower, left-hand corner;

FIG. 15 is a perspective view of the rear of the carrier;

FIG. 16 is a front elevational view of the carrier;

FIG. 17 is a cross-sectional view taken generally along the plane 17—17 in FIG. 16;

FIG. 18 is a cross-sectional view taken generally along the plane 18—18 in FIG. 16;

FIG. 25 is a side elevational view of the assembly of the carrier, flag, connecting arm, and crank, and the assembly is viewed generally along the plane 25—25 in FIG. 9 with the other components of the pump omitted purposes of clarity;

FIG. 25A is a cross-sectional view taken generally along the plane 25A—25A in FIG. 25;

FIG. 26 is a perspective view of the skirt removed from the pump in an orientation as it would appear if it were in the pump and viewed from the front, upper, left-hand corner of the pump;

FIG. 27 is a perspective view of the skirt shown from the rear;

FIG. 30 is a top plan view of the chassis;

FIG. 31 is a perspective view of the door handle; and

FIG. 32 is another perspective view of the door handle.

DESCRIPTION OF THE PREFERRED EMBODIMENT

Figure 3:
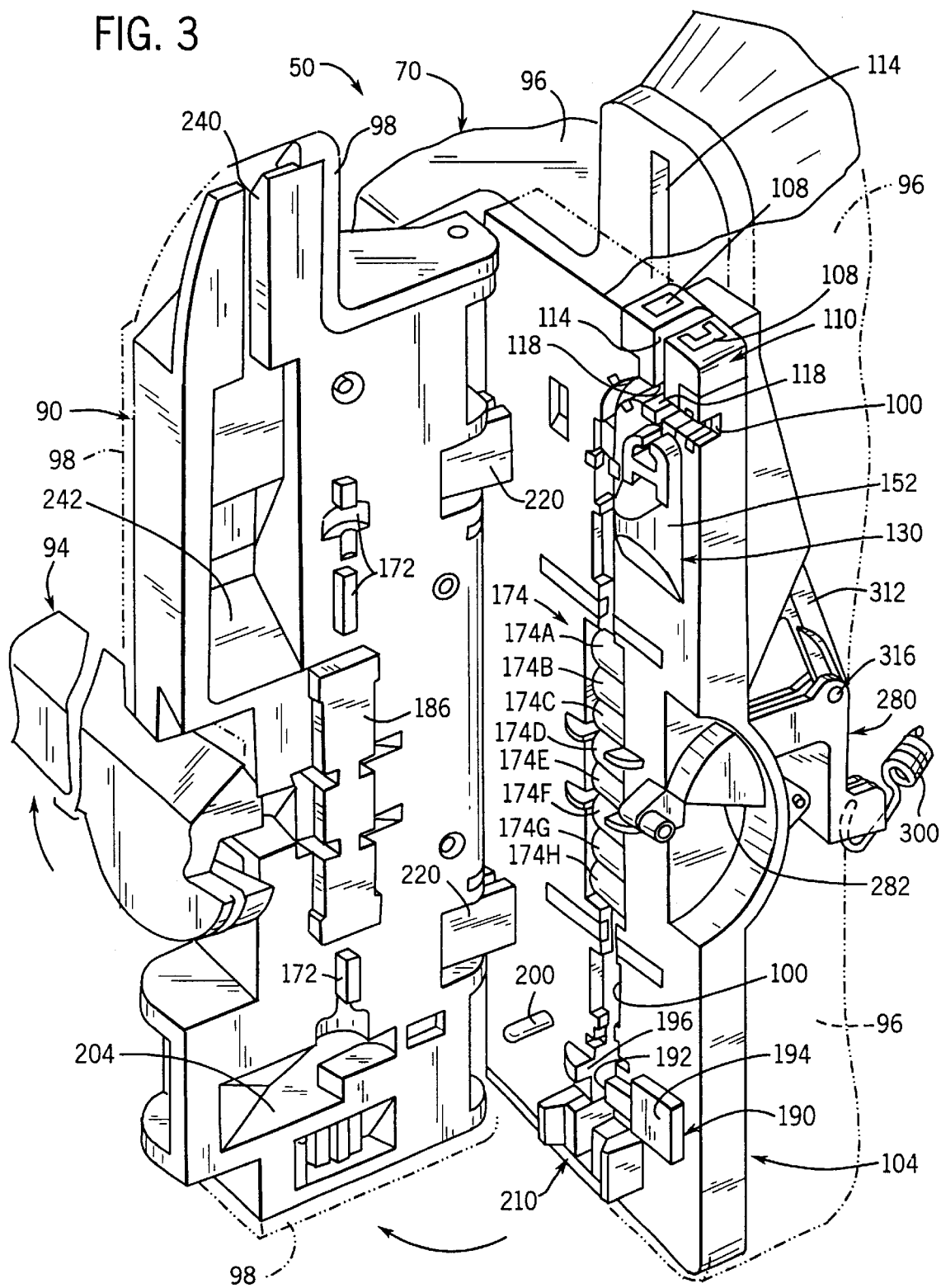
FIG. 3 is an enlarged, fragmentary, perspective view of the front of the infusion pump shown in FIG. 2.

While this invention is susceptible of embodiment in many different forms, this specification and the accompanying drawings disclose only one specific form as an example of the invention. The invention is not intended to be limited to the embodiment so described, however. The scope of the invention is pointed out in the appended claims.

For ease of description, a pump incorporating features of this invention is described in one normal (upright) orientation, and terms such as upper, lower, horizontal, etc., are used with reference to this orientation. It will be understood, however, that the pump of this invention may be stored, transported, and sold in an orientation other than the orientation described.

Figures illustrating the pump show some mechanical elements that are known and that will be recognized by one skilled in the art. The detailed descriptions of such elements are not necessary to an understanding of the invention, and accordingly, are herein presented only to the degree necessary to facilitate an understanding of the novel features of the present invention.

The pump incorporating features of this invention is used with certain conventional components the details of which, although not fully illustrated or described, will be apparent to those having skill in the art and an understanding of the necessary functions of such components.

The improved system of the present invention accommodates delivery of a fluid to a patient with a variety of standard, intravenous administration sets, one of which is illustrated in FIG. 1 and is designated generally therein by the reference numeral 40. The administration set 40 is typically employed to deliver parenteral fluids, enteral fluids, whole blood, red blood cell components, and the like from a fluid container, such as a bottle or such as a flexible bag 42 which is shown in FIG. 2 supported on an intravenous administration stand 44. A portion of the administration set 40 is engaged by a peristaltic pump 50, and a distal portion of the administration set 40 downstream of the pump 50 can be connected to a patient's indwelling vein access device, such as a needle or cannula (not illustrated) which is inserted into the patient.

The container 42 may be of any suitable conventional or special design. The detailed design and specific structure of the container 42 form no part of the present invention.

The administration set 40 may be of any appropriate conventional or special design. The set 40 illustrated in FIG. 1 is a primary, vented, intravenous set sold in the U.S.A. under the designation No. 1881 by Abbott Laboratories, 100 Abbott Park Road, Abbott Park, Ill. 60064-3500, U.S.A. The administration set 40 has a proximal end defined by a hollow, piercing pin 46 projecting from a conventional bacterial retentive air filter 48 at the upper end of a drip chamber 52. A length of hollow, flexible tubing 54 extends from the bottom of the drip chamber 52 through a roller clamp 56 of the type sold by Abbott Laboratories under the designation CAIR.

Disposed on the tubing 54 downstream of the roller clamp 56 is a slide clamp 60 of the type sold by Abbott Laboratories under the designation DUO SLIDE. The DUO SLIDE clamp 60 is described in more detail hereinafter.

A conventional Y-injection site 62 is provided on the tubing 54 downstream of the slide clamp 60. The distal end of the tubing 54 is provided with a conventional male adaptor 64. The adaptor 64 is designed to be attached to a venipuncture device.

The administration set components may be of any suitable special or conventional design, the details of which form no part of the present invention except that some features of a preferred embodiment of the invention are designed to accommodate, and cooperate with, conventional, flexible tubing 54 and with the slide clamp 60 having the structure as embodied in the above-identified DUO SLIDE clamp 60. The structure of DUO SLIDE clamp 60 is described in more detail hereinafter.

As shown in FIG. 2, the pump 50 includes a housing 70 and a rearwardly projecting mounting clamp 72 by which the pump 50 can be mounted to the stand 44. The clamp 72 includes a manually operable knob 73. A convenient carrying handle 74 projects upwardly from the top of the housing 70. Electric power is provided through the rear of the pump via a power cord 71.

The pump 50 has a front panel 76 containing a liquid crystal display screen device 78 and a key pad 80. Next to the front panel 76 is a front door 90 on which is mounted a door handle 94. As shown in FIG. 3, the door 90 can be opened about 90° by initially pivoting the handle 94 from a substantially vertical orientation (as shown in FIG. 2) to a substantially horizontal orientation (as shown in FIG. 3) to unlatch the door 90 from the housing 70, and then swinging the door 90 outwardly.

In FIG. 3, the open pump 50 is shown with the tubing 54 removed so as to better illustrate the details of the pump structure. Further, as seen in FIG. 3, the housing 70 includes an exterior covering or shell 96 which is partly shown in phantom by dashed lines so as to reveal interior details. Similarly, in FIG. 3, the door 90 has an exterior cover or shell 98 which is shown partly in phantom by dashed lines to better illustrate interior details.

Figure 4:
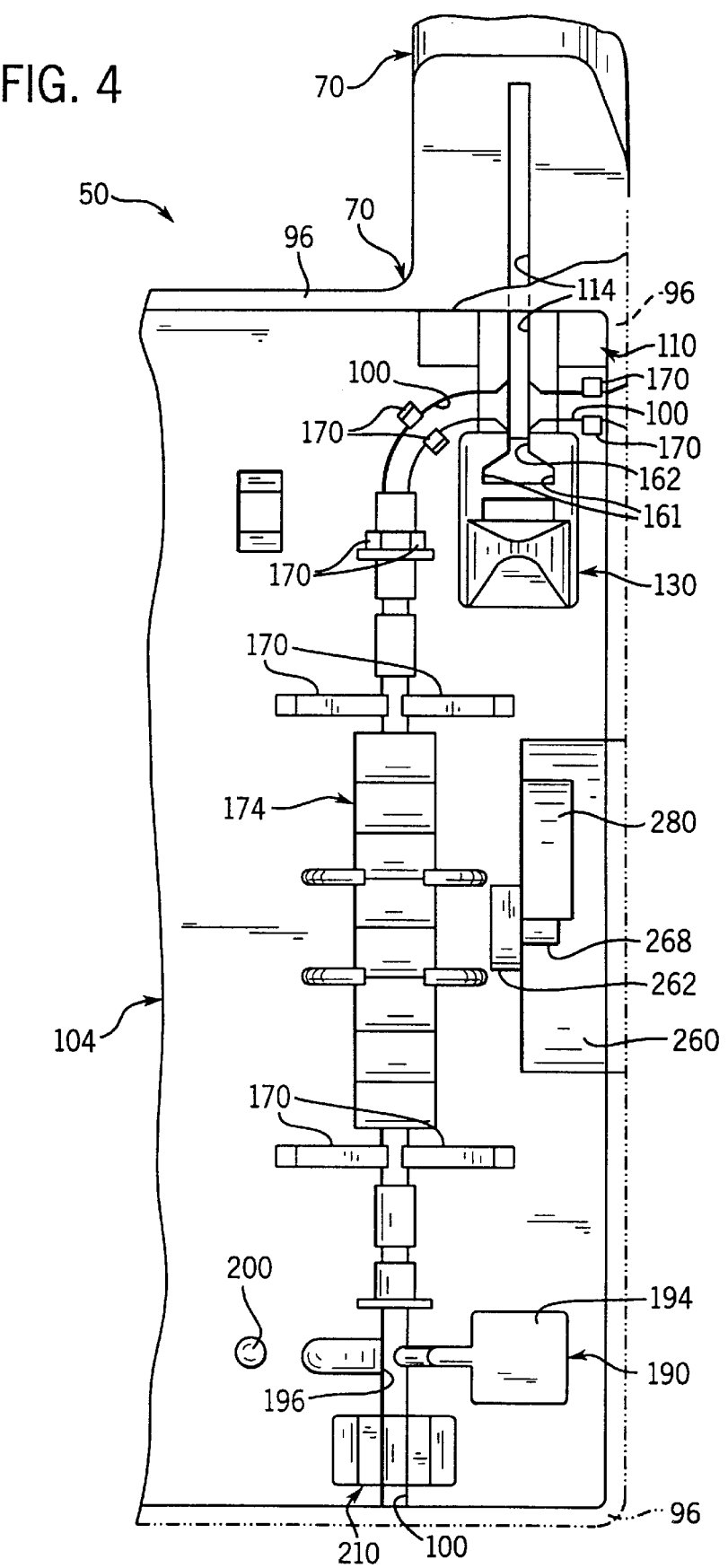
FIG. 4 is a fragmentary, front elevational view of the pump shown in FIG. 3.
Figure 6:
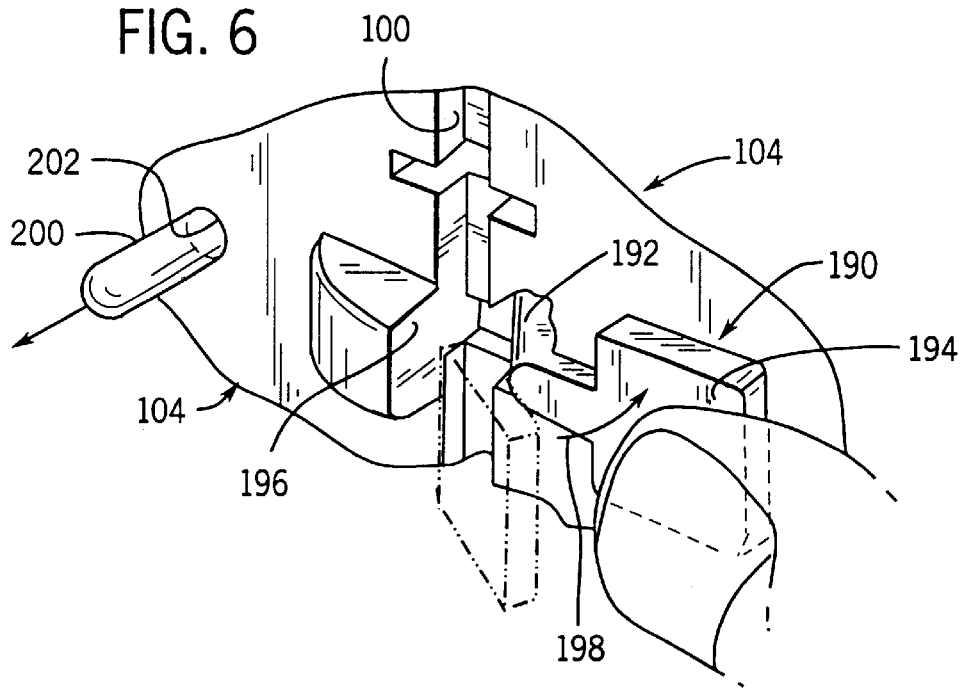
FIG. 6 is a greatly enlarged, fragmentary, perspective view of a lower portion of the pump tubing-receiving region showing the operation of the anti-flood clamp.
Figure 7:
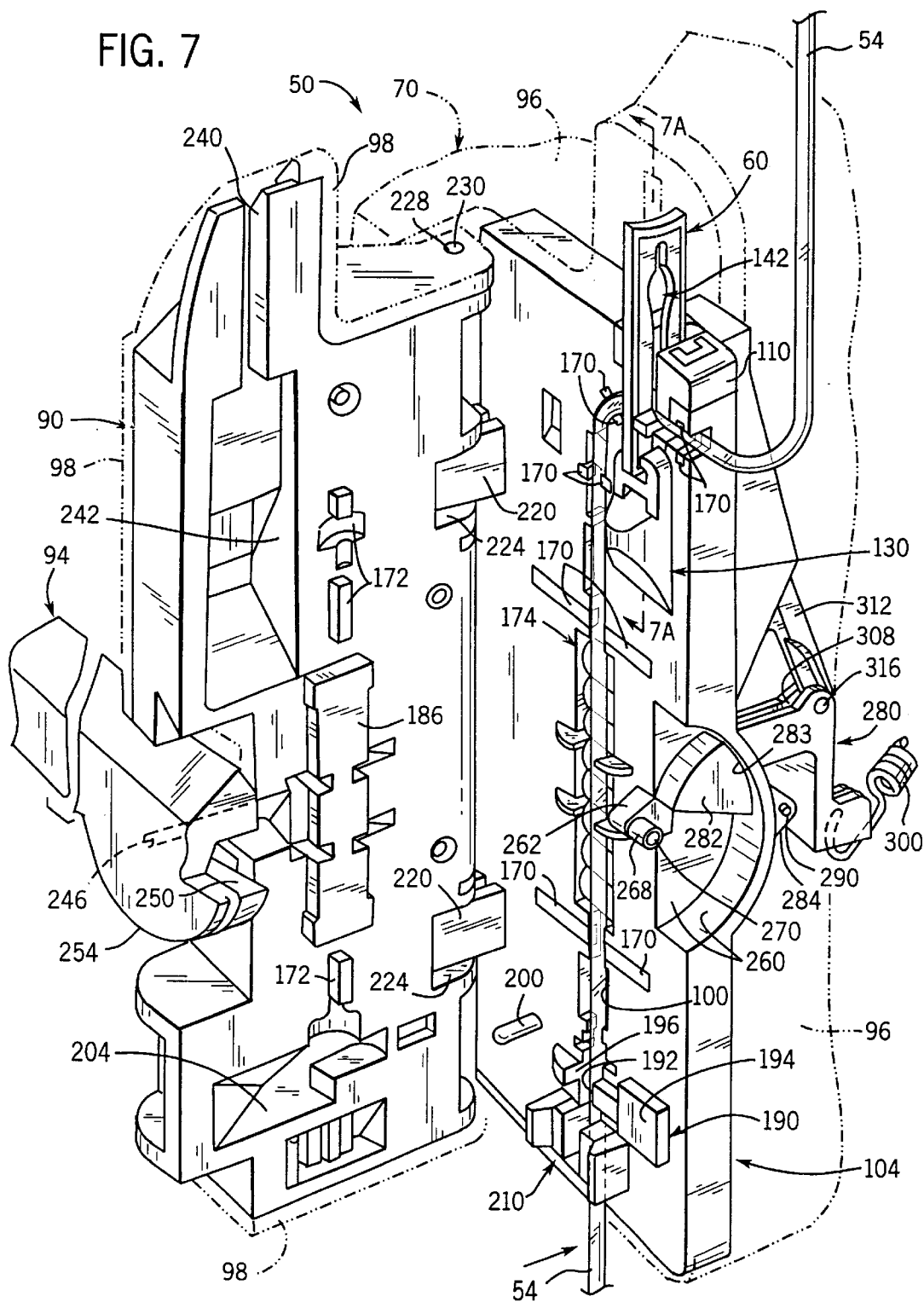
FIG. 7 is a fragmentary, perspective view similar to FIG. 3, but FIG. 7 shows the administration set tubing loaded into the pump.

As shown in FIGS. 3 and 4, the open face of the pump housing 70 defines a receiving path 100 for receiving the administration set tubing 54 which is shown loaded in the pump housing 70 in FIG. 7. The receiving path 100 is defined along a generally planar, front, inside face of the open pump housing 70. In particular, the pump 50 includes a block or chassis 104 (FIGS. 3–7) which may be characterized as generally defining a part of the housing 70 to which other pump components are mounted. The chassis 104 includes various cavities and apertures for receiving such other components which are mounted to the chassis or which coact with the chassis 104 as described in detail hereinafter.

As shown in FIGS. 3 and 4, the receiving path 100 in the upper right-hand corner of the chassis 104 is oriented generally horizontally and opens outwardly to the right-hand side of the pump 50 through the exterior shell 96. The exterior shell 96 thus defines an inlet portion of the receiving path 100, and the exterior shell 96 may be characterized as also generally forming part of the pump housing 70.

Figure 28:
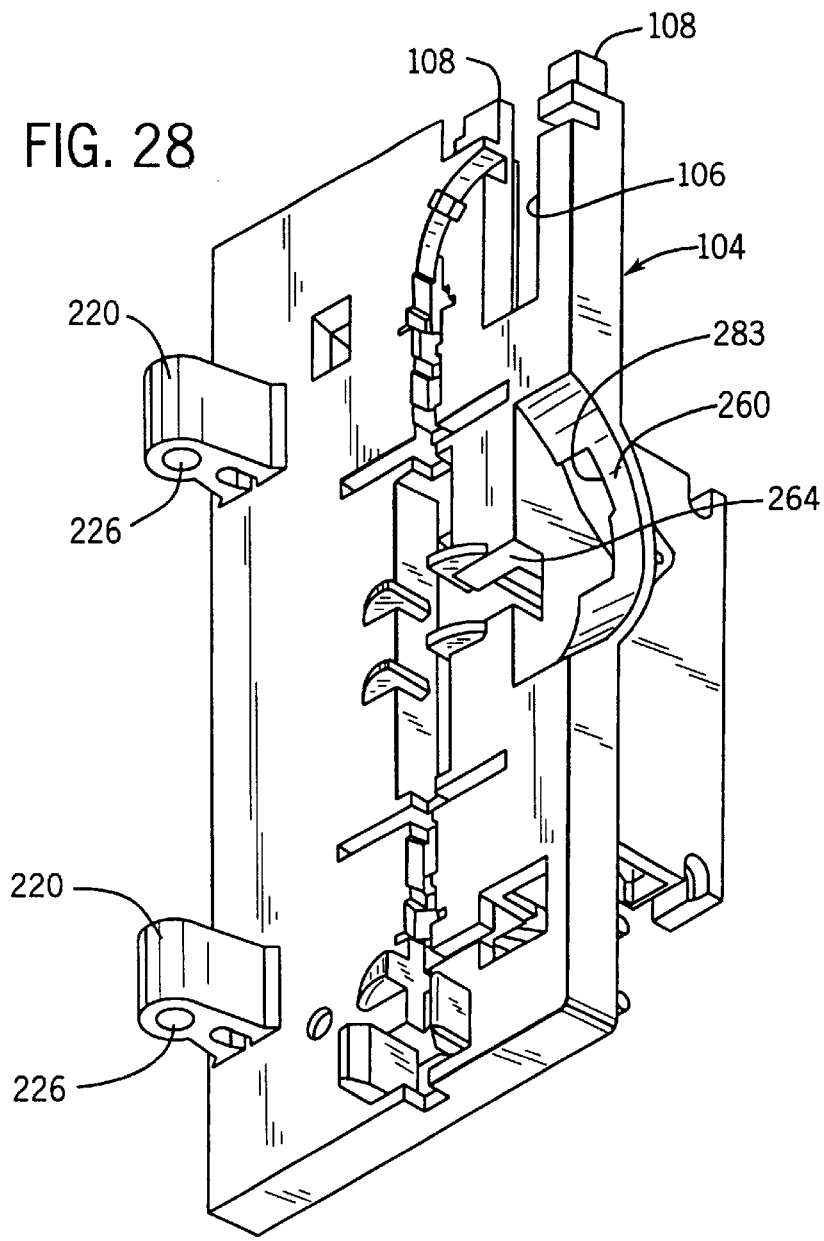
FIG. 28 is a perspective view of the chassis for receiving the administration set tubing and to which various pump components (not shown) are mounted, and the chassis is shown removed from the pump in an orientation as it would appear if it were in the pump and viewed from the front, lower, right-hand corner of a pump.
Figure 28A:
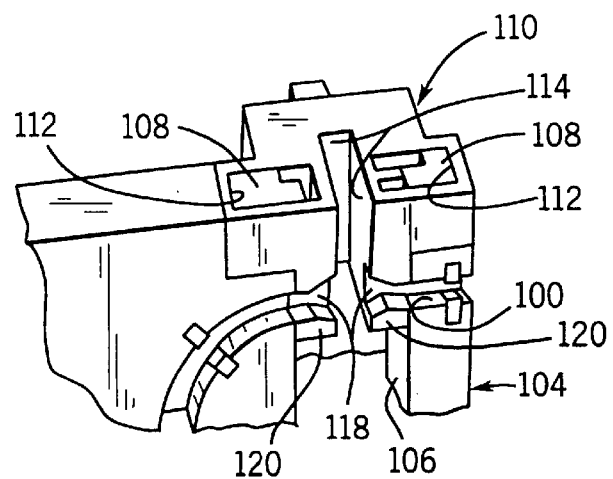
FIG. 28A is a fragmentary, perspective view of the front, upper, right-hand corner of the chassis with the skirt assembled thereto.
Figure 29:
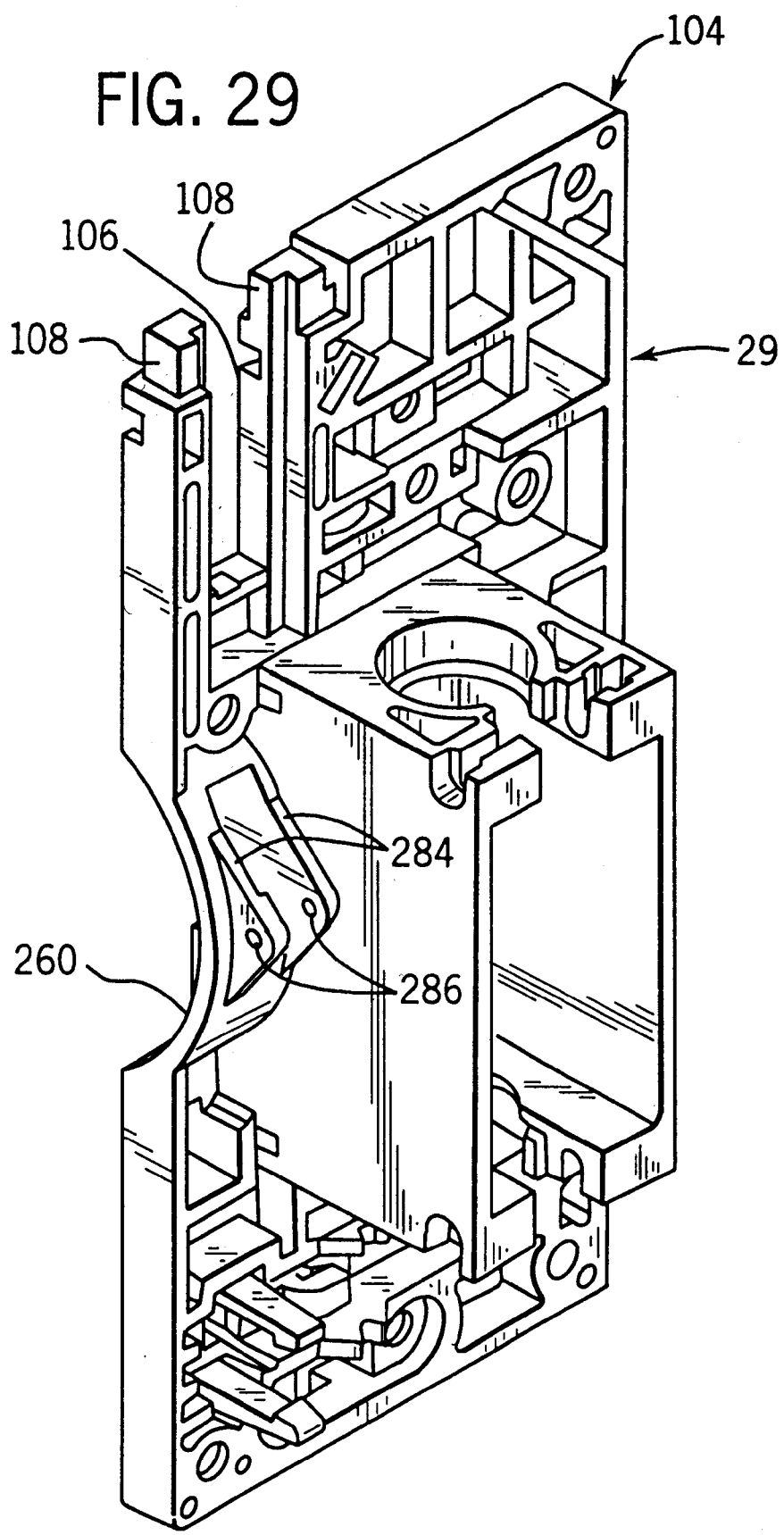
FIG. 29 is a rear perspective view of the chassis.

The chassis 104 is illustrated separately in FIGS. 28, 29, and 30. The upper right-hand corner of the chassis 104 defines a vertically oriented slot 106. At the upper end of the slot 106, on each side of the slot, the chassis 104 defines upwardly projecting posts 108 to which are mounted an insert block or skirt 110. The skirt 110 is shown separately in FIGS. 26, 27. The skirt 110 defines a pair of receiving apertures 112. Each aperture 112 receives one of the chassis posts 108 as shown in FIG. 28A. The skirt 110 can be further secured to the chassis 104 with screws (not illustrated) through screw-receiving bores 113 (FIGS. 26 and 27).

Figure 5:
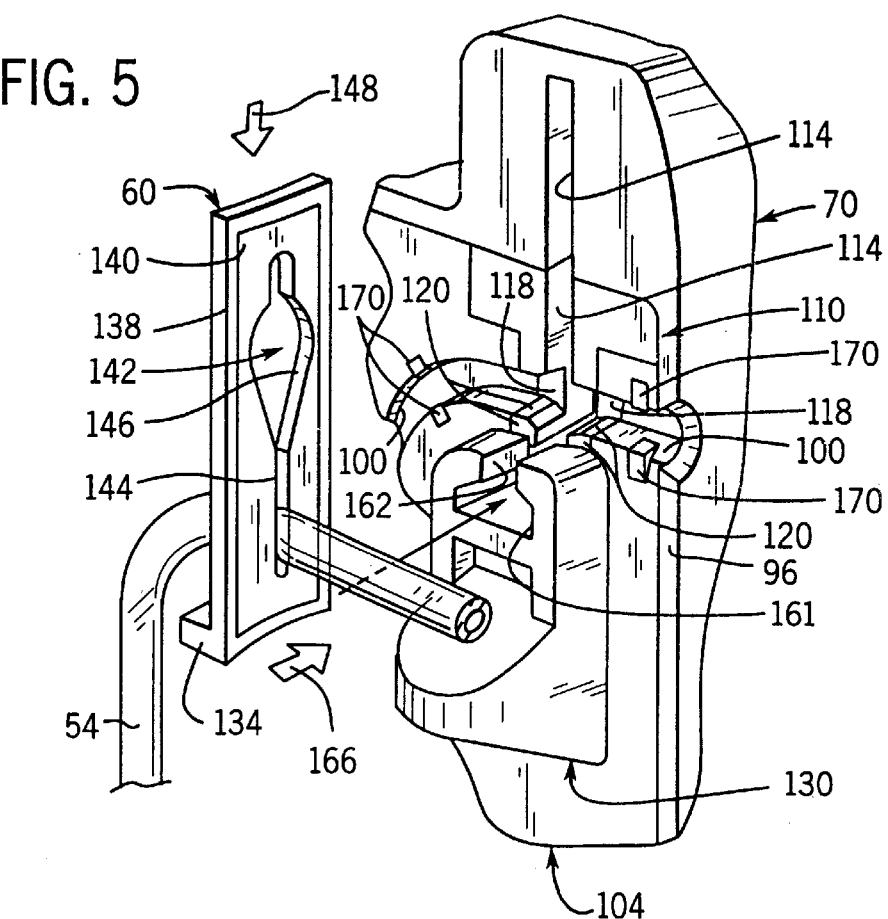
FIG. 5 is a greatly enlarged, fragmentary, perspective view of an upper portion of the tubing-receiving path of the pump showing how a portion of the tubing with a slide clamp disposed thereon is inserted into the pump.

The front of the skirt 110 defines a vertical groove 114 which communicates with the horizontal portion of the tubing receiving path 100 as can be seen in FIGS. 3, 4, 5, 9, and 28A. As shown in FIGS. 5, 26, and 28A, the upper, front portion of the skirt 110 defines an inwardly extending notch 118 on either side of the vertical groove 114, and the notch 118 defines a part of the receiving path 100 in the face of the pump.

The bottom of the notch 118 at the front of the skirt 110 is defined by a pair of spaced-apart support ledges 120 which define between them a continuation of the vertical groove 114 (FIG. 5). The top surfaces of the ledges 120 form bottom portions of the tubing receiving path 100 on either side of the vertical groove 114. The vertical groove 114 extends upwardly into the housing 70 above the skirt 110 as illustrated in FIGS. 3, 4, 5, and 9.

Figure 7A:
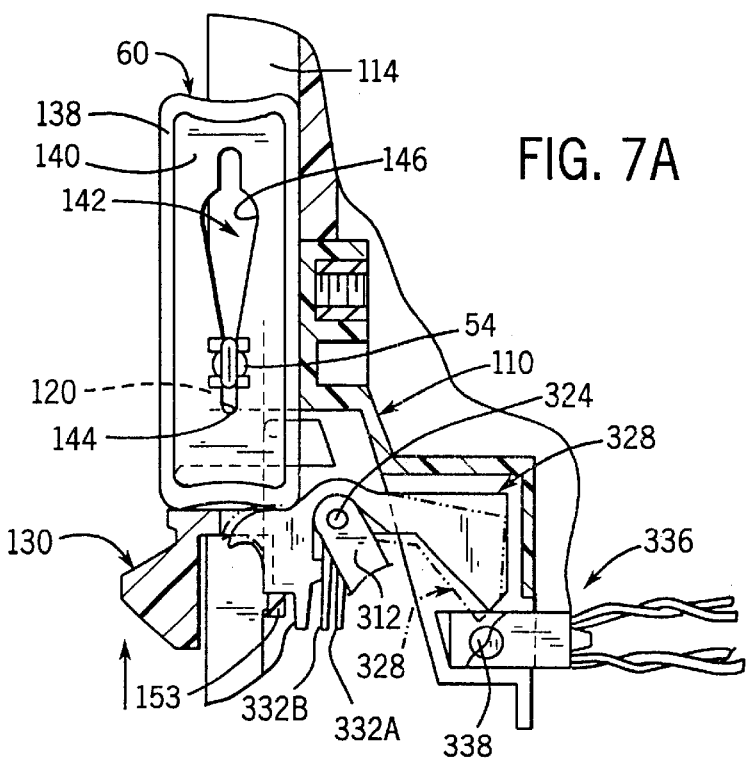
FIG. 7A is a greatly enlarged, fragmentary, cross-sectional view taken generally along the plane 7A—7A in FIG. 7.
Figure 7B:
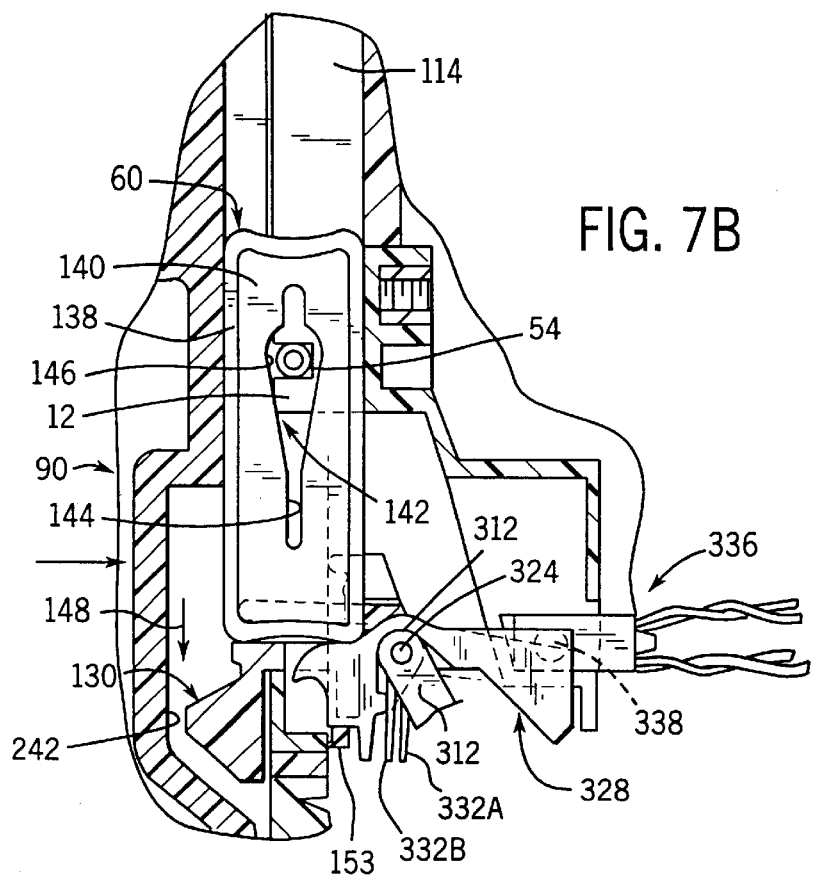
FIG. 7B is a view similar to FIG. 7A, but FIG. 7B shows a moved position of the slide clamp wherein the slide clamp is in an open condition relative to the tubing.
Figure 10:
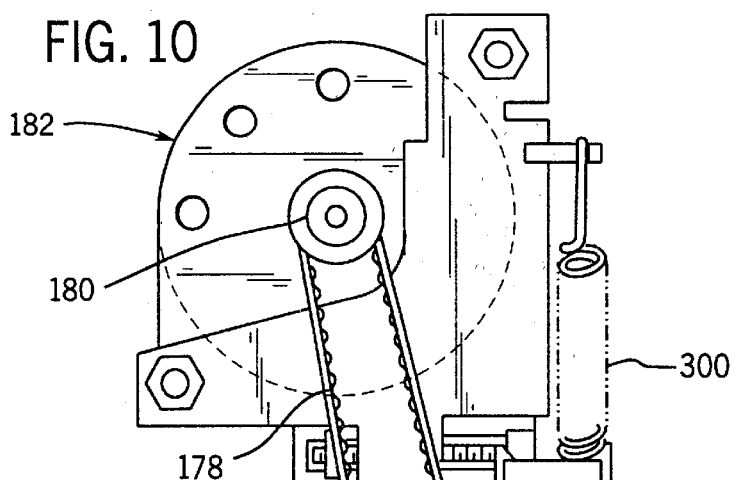
FIG. 10 is a fragmentary, cross-sectional view of a portion of the pump.
Figure 10A:
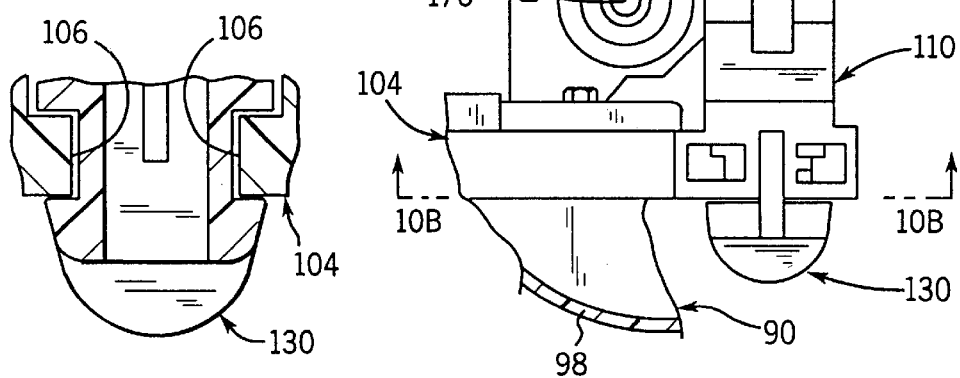
FIG. 10A is a fragmentary, front elevational view taken generally along the plane 10A—10A in FIG. 9.
Figure 10B:
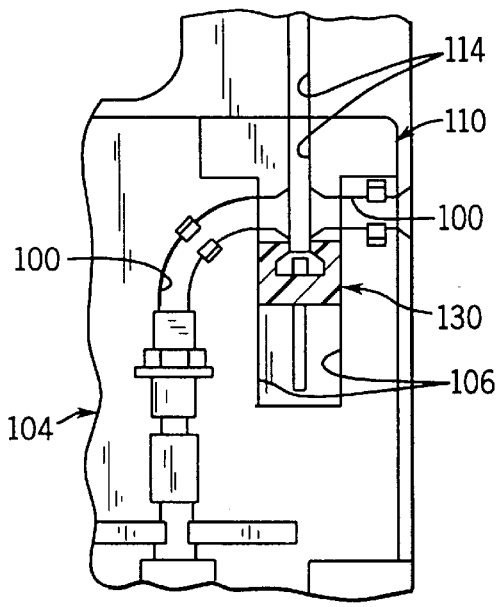
FIG. 10B is a fragmentary, cross-sectional view taken generally along the plane 10B—10B in FIG. 10 showing the carrier moved to a lower position when the door is closed.
Figure 10C:
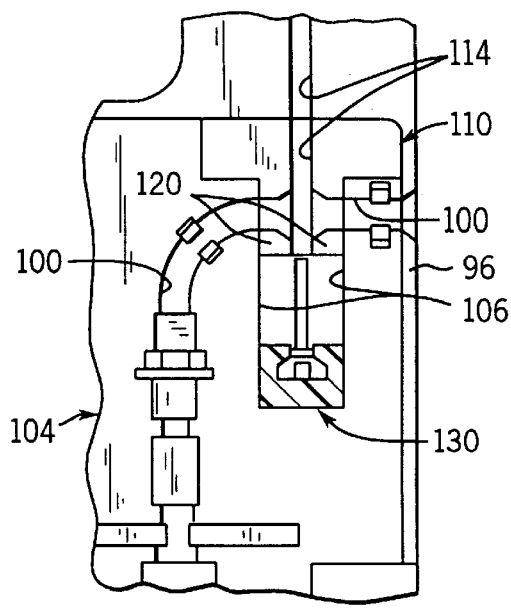
FIG. 10C is a view similar to FIG. 10B, but FIG. 10C shows the carrier moved to the elevated position when the door is opened.
Figure 11:
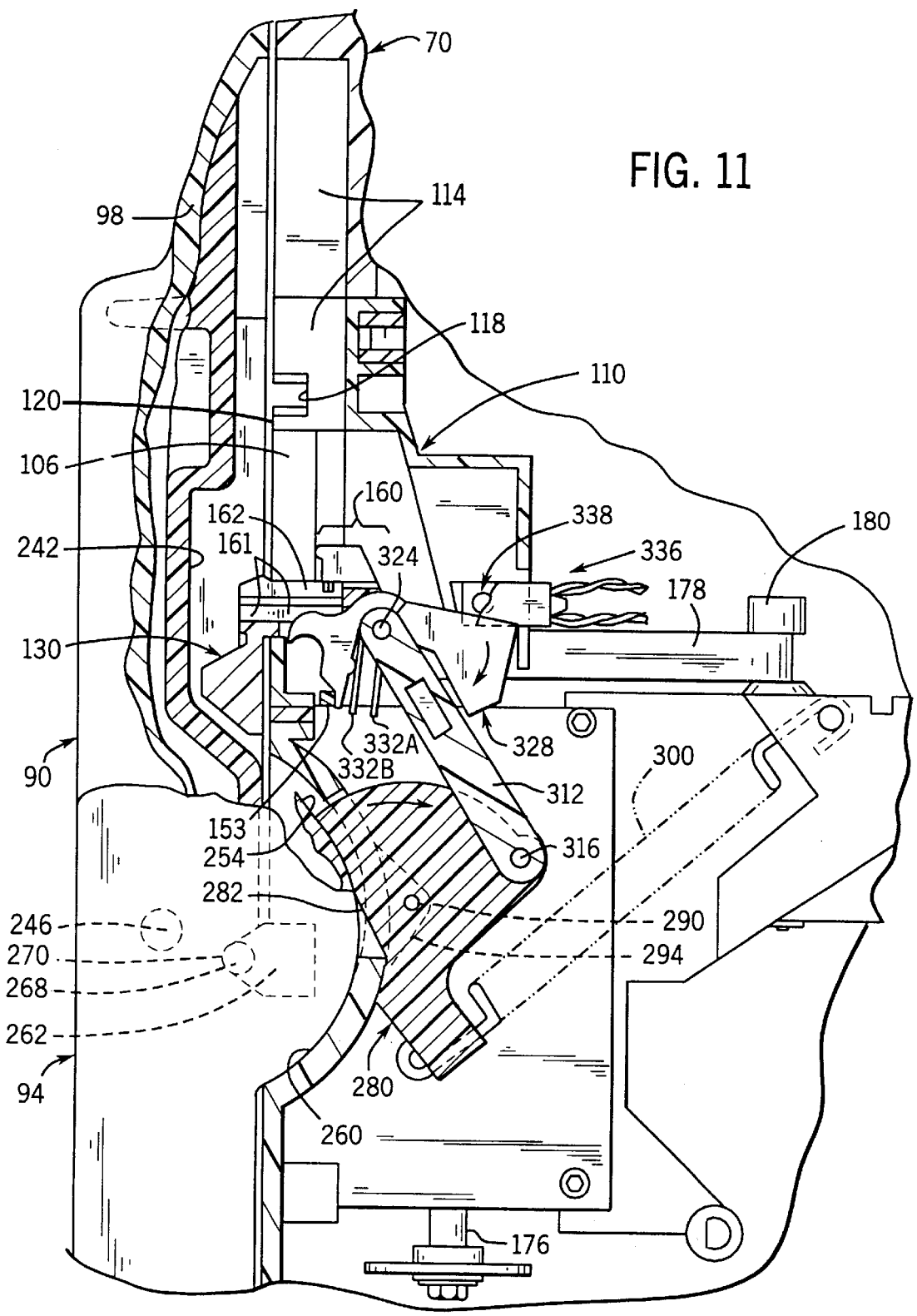
FIG. 11 is an enlarged, fragmentary, side elevational view partly in cross section taken generally along the plane 11—11 in FIG. 9.

As can be seen in FIG. 28A, the chassis slot 106 below the skirt ledges 120 is relatively wide. The slot 106 is adapted to receive a carrier means for holding a tubing clamp. In the preferred embodiment, the carrier means includes a slide clamp carrier 130 which holds the slide clamp 60 and which is adapted to move between (1) an elevated or raised position as shown in FIGS. 7, 7A, and 10C, and (2) a lowered position as shown in FIGS. 7B, 10B, and 11. In FIGS. 10B, 10C, and 11, the slide clamp 60 and tubing 54 are omitted to better illustrate details of the carrier and other components of the housing 70. The mechanisms for effecting movement of the carrier 130 between the upper, elevated position (shown in FIGS. 3, 4, 5, 7, 7A, and 10C) and the lowered position (illustrated in FIGS. 7B, 10B, 11, and 12) are described in detail hereinafter.

The carrier 130 is adapted to receive and hold the slide clamp 60 in a generally vertical orientation as illustrated in FIGS. 5 and 7. The slide clamp 60 has a lower end defined by a laterally extending foot 134 (FIG. 5). Projecting upwardly from the foot 134 is an elongate, four-sided frame 138 surrounding a slightly thinner, generally planar, web 140. The web 140 defines an elongate aperture 142 having a lower, narrow portion 144 and an upper, wide portion 146.

Prior to the tubing 54 and slide clamp 60 being inserted into the pump 50, the clamp 60 is initially disposed on the tubing 54 in an orientation wherein the tubing 54 is located in the narrow portion 144 of the clamp aperture 142 so as to be squeezed into a closed configuration occluding flow therethrough (FIG. 5). The slide clamp 60 is adapted to accommodate subsequent movement downwardly (in the direction of the arrow 148 in FIG. 5) relative to the tubing 54, after the clamp 60 is inserted into the carrier 130. The downward movement is generally perpendicular to the longitudinal axis of that portion of the tubing 54 adjacent the clamp 60 so as to position the wide portion 146 of the clamp aperture 142 about the tubing 54 (FIG. 7B). Movement of the carrier 130 downwardly (in the direction of the arrow 148 as shown in FIG. 7B) from the elevated position (illustrated in FIGS. 5 and 7A) to the lowered position (illustrated in FIG. 7B) carries the slide clamp 60 downwardly relative to the tubing 54 which is held in the tubing receiving path on the ledges 120 above the carrier 130. The mechanisms for moving the clamp 60 in the carrier 130 downwardly are described in detail hereinafter.

The carrier 130 has a configuration adapted to permit convenient insertion of the clamp 60 into the carrier 130. The carrier 130 includes a front portion 152 (FIGS. 13–18) which projects beyond the front face of the housing chassis 104 as shown in FIGS. 3 and 7. The front portion 152 is wider than the chassis slot 106 (FIG. 10B).

The carrier 130 includes a reduced width, intermediate portion 156 (FIGS. 13–15, 17, and 18). The reduced width, intermediate portion 156 extends through the chassis slot 106.

The carrier 130 includes a wider, rear portion 160. The wider, rear portion 160 is disposed along the rear, vertical surface of the chassis 104 along the chassis slot 106. The carrier 130 is initially mounted in the chassis slot 106 during assembly of the pump components prior to mounting the skirt 110 over the top of the chassis slot 106 as shown in FIG. 28A. The carrier 130 is adapted to reciprocate vertically within the chassis slot 106. The bottom, front edge of the carrier rear portion 160 includes a bridging rib 153

(FIGS. 11, 13, 14, 17, and 18) and a slot 155 (FIGS. 15 and 17) behind the bridging rib 153.

The carrier 130 defines a first slot 161 (FIGS. 13 and 16) extending through the front portion 152, through reduced width intermediate portion 156, and partway through the rear portion 160 as can be seen in FIG. 17. The first slot 161 has a configuration adapted to receive the bottom end of the slide clamp 60, including the outwardly projecting foot 134 (FIG. 5). The bottom of the carrier slot 161 in the carrier rear portion 160 communicates with the top of the rear portion slot 155 as shown in FIG. 17.

The carrier 130 has a second slot 162 which extends from, and which is generally normal to, the first slot 161. The second slot 162 is adapted to receive the vertical, upwardly extending portion of the slide clamp 60 which projects above the foot 134 when the slide clamp 60, along with the tubing 54 disposed therein, is inserted into the carrier 130 (in the direction of the arrow 166 (FIG. 5)). The carrier 130 includes detents 162A and 162B (FIGS. 13 and 16) along the surface that defines the second slot 162. These detents 162A and 162B are used to grip the bottom portion of the frame 138 of the slide clamp 60 when the slide clamp 60 is inserted into the carrier 130 as shown in FIG. 7. The carrier vertical slot 162 is aligned in registry with the vertical groove 114 defined by the chassis skirt 110 and by the upper portion of the housing 70 as shown in FIG. 5.

When the slide clamp 60 is fully inserted into the carrier 130, the tubing 54 is received within the channel defining the receiving path 100 on either side of the vertical groove 114. The chassis 104 includes pairs of opposed tabs 170 (FIG. 5) which project slightly into the channel of the receiving path 100 so as to grip the tubing 54 (FIG. 7) by effecting a small, local deformation of the tubing adjacent the tabs 170. The tabs 170 are preferably separately molded insert pieces which are mounted in appropriate receiving cavities within the chassis 104. A number of such pairs of confronting tabs 170 are provided along the receiving path 100 as shown in FIG. 4.

A peristaltic pump head 174 is disposed along the vertical portion of the tubing receiving path 100 as shown in FIGS. 3, 4, and 7. The peristaltic pump head 174 may have any suitable conventional or special configuration. The peristaltic pump head 174 typically comprises a plurality of keys, such as keys 174A–174H, which are sequentially engaged and moved outwardly against the tubing by cam sections on a crank shaft 176 (FIG. 10) which is vertically disposed behind the keys within the pump housing 70. The crank shaft 176 is rotated by a timing belt driven from a shaft 180 of a stepping motor 182 (FIG. 10). A platen 186 is mounted in the door 90 and confronts the tubing 54 adjacent the pump head 174 when the door 90 is closed.

Each pump head key 174A–174H, as it is moved outwardly against the tubing 54, forces the tubing 54 against the platen 186 (FIG. 3) on the closed door 90. The platen 186 is biased toward the pump head 174 by a spring (not visible) acting between the door and the platen 186. As one key 174A–174H is moved outwardly to squeeze the tubing 54 closed against the platen 186, the next, adjacent downstream key is moved outwardly to force the fluid contained within the tube further downstream in the tubing 54 in a peristaltic action. The peristaltic pumping system, including the above-discussed peristaltic pump system elements 174A–174H, 176, 178, 180, 182, and 186, may be of any suitable conventional or special design. The detailed design and operation of such peristaltic pumping system components, as well as other supporting components, control systems, etc., form no part of the present invention.

The tubing 54 extends below the pump head 174 within the channel defining the tubing receiving path 100. The tubing 54 extends through an anti-flood clamp 190 near the bottom of the pump. The anti-flood clamp 190 includes an engaging rib 192 and a laterally extending finger press pad 194 (FIG. 6). Adjacent the engaging rib 192, on one side of the tubing receiving path 100, is an anvil 196 projecting outwardly from the front surface of the chassis 104. The tubing 54 is normally loaded between the anvil 196 and the engaging rib 192 as shown in FIG. 7.

A portion of the anti-flood clamp 190 extends behind the chassis 104 and includes a spring-biased, over-center toggle spring latch mechanism (not visible in the figures). Normally, when the pump door 90 is open, the anti-flood clamp rib 192 is biased to the closed position (illustrated by solid lines in FIGS. 3 and 7, and shown in phantom by dashed lines in FIG. 6).

In order to load the tubing 54 into the tubing receiving path 100 between the anvil 196 and the tubing engaging rib 192, the finger press pad 194 is pressed rearwardly toward the chassis 104 (in the direction of the arrow 198 as shown in FIG. 6). When the finger press pad 194 is pushed rearwardly to the point where it is substantially parallel to, and adjacent, the surface of the chassis 104, the over-center toggle spring latch mechanism behind the chassis 104 holds the anti-flood clamp 190 in the open position—even after the finger is removed from the finger press pad 194. This establishes clearance between the engaging rib 192 and the anvil 196 to accommodate positioning of the tubing 54 between the rib 192 and the anvil 196.

When the anti-flood clamp is in the fully opened position illustrated by solid lines in FIG. 6, a portion of the latch mechanism (not visible behind the chassis 104) is forced forwardly so as to extend a pin 200 from a bore 202 in the face of the chassis 104. When the door 90 is subsequently closed, a portion of the door 90 engages the distal end of the pin 200 and forces it inwardly in the bore 202. Inward movement of the pin 200 (through its attachment to the anti-flood clamp 190 behind the chassis 104) causes the flood clamp 190 to pivot outwardly just beyond the over-center point of the toggle spring mechanism toward the closed position, but the closed door 90 has a recessed engaging surface 204 which prevents the finger press pad 194 and rib 192 from moving to the fully closed position that would squeeze the tubing closed. This permits fluid flow through the clamp 190 when the door is closed. However, when the door 90 is subsequently opened, the finger pad 194 and rib 192 are free to move completely to the fully closed position under the influence of the toggle spring mechanism so as to clamp the tubing closed.

The anti-flood clamp 190 described above may be of any suitable special or conventional design. The incorporation of an anti-flood clamp 190, and the detailed design and operation thereof, form no part of the present invention.

If desired, the pump 50 may include an air sensor assembly, such as the air sensor assembly 210 below the anti-flood clamp 190 as illustrated in FIGS. 3, 4, and 7. The air sensor assembly 210 may be of any suitable special or conventional design for sensing the presence of air bubbles within the tubing 54. Typically, the sensor assembly 210 includes a piezoelectric sensor around a slot that defines part of the tubing receiving path 100. The incorporation of an air sensor assembly 210, and the detailed design and operation thereof, form no part of the present invention.

The pump 50 may include other sensors, switches, alarms, etc., as may be suitable or desired, but such other elements form no part of the present invention.

As illustrated in FIG. 3, the inside surface of the door 90 may include a plurality of projections 172 which align with the channel defining the tubing receiving path 100 when the door 90 is closed and which function to push the tubing 54 into the channel defining the receiving path 100.

The tubing 54 can be easily loaded into the above-described tubing receiving path 100 in the pump 50. Typically, before the administration set tubing is loaded into the pump 50, the container 42 (FIG. 2) is connected to the tubing 54. Prior to connecting the tubing 54 to the container 42, the roller clamp 56 (FIG. 1) is first closed to occlude flow through the tubing 54. Then the outlet on the container 42 (FIG. 2) is exposed. The administration set piercing pin 46 (FIG. 1) is then inserted into the outlet of the container 42 with a twisting motion. The container 42 is then suspended from the stand 44, and the drip chamber 52 (FIG. 1) is filled to the score mark.

Before the tubing 54 is loaded into the pump 50, the administration set 40 is primed. With the pump 50 located below the container 42, the roller clamp 56 is opened to expel air from the administration set tubing 54 while the slide clamp 60 located on the tubing is in an open condition so as not to occlude the tubing. The roller clamp 56 is then closed. The male adapter 64 at the distal end of the administration set tubing 54 can then be attached to a venipuncture device. If the venipuncture device is not indwelling, then the device must primed prior to making the venipuncture.

Care should be taken to purge air bubbles from the system. Air is dislodged from the back check valve in the Y-site 62 by inverting and tapping it sharply while fluid is flowing.

Prior to loading the tubing 54 into the pump 50, the operator should verify that the roller clamp 56 is between the container 42 and the slide clamp 60. The operator should also verify that the roller clamp 56 is closed and confirm that there is no flow in the drip chamber 52. Next, the slide clamp 60 is closed by pushing the clamp 60 so that the tubing 54 is squeezed closed in the narrow portion 144 of the clamp aperture.

Then the pump door 90 is opened by lifting the door handle 94. The anti-flood clamp 190 is then opened by pushing the finger press pad 194 (in the direction of the arrow 198 as shown in FIG. 6). The clamp 190 will remain open after the operator's finger is removed owing to the action of the over-center toggle spring mechanism with the clamp 190 as described above.

The administration set tubing 54 is then positioned along the open face of the pump 50. The slide clamp 60 is aligned with the carrier slots 161 and 162 as illustrated in FIG. 5. The slide clamp 60, along with the closed tubing 54 disposed therein, is moved inwardly (in the direction of arrow 166 as shown in FIG. 5) so as to position the slide clamp 60 within the carrier slots 161 and 162 and within the housing vertical groove 114. This results in the portion of the tubing 54 adjacent the slide clamp 60 being received within the channel defined in the tubing receiving path 100 above the carrier 130.

The operator then aligns the remaining portion of the tubing 54 adjacent the remaining portions of the receiving path 100, and the operator loads the tubing 54 within the channel of the receiving path 100 from the top to the bottom of the pump. Care should be taken so as not to stretch the tubing. The tubing 54 is pressed into the channel defining the receiving path 100 with the pad of a finger tip while avoiding contacting the tubing with sharp objects, such as finger nails.

The door 90 is then closed over the loaded tubing 54, and the handle 94 is latched by pushing it downwardly to the fully closed position illustrated in FIGS. 1 and 11. Next, before starting the pump 50, the roller clamp 56 above the pump 50 should be opened, and the lack of flow into the drip chamber 52 should be confirmed.

With reference to FIG. 7 (which shows the administration set tubing 54 loaded in the pump 50), it will be appreciated that in the illustrated preferred form of the pump, the tubing receiving path is defined substantially in a plane along the housing 70 (which housing 70 includes the chassis 104 and the top skirt 110 that define the channel of the tubing receiving path). The plane in which the loaded tubing 54 lies is generally vertical when the pump is in the normal operating orientation. The clamp carrier 130 is movable between the elevated position (FIGS. 7, 7A, and 10C) and the lowered position (FIGS. 7B, 9 and 10B) in a direction that is parallel to the plane defined by the tubing receiving path.

Further, it will be appreciated that the pump 50 is adapted to be disposed in a normal operating orientation, as shown in FIGS. 3, 4, and 7, wherein the pump has (1) a middle portion that includes the pump head 174, (2) an upper portion that extends above the pump head and that includes the carrier 130, and (3) a lower portion that extends below the pump head 174 and that can include the anti-flood clamp 190 (if provided) and the air sensor 210 (if provided)). In the illustrated preferred embodiment, the tubing receiving path is oriented substantially in a plane which is generally vertical when the pump is in the normal operating orientation. Further, the portion of the receiving path (and tubing) along the pump head 174 lies generally in a straight line.

Figure 9:
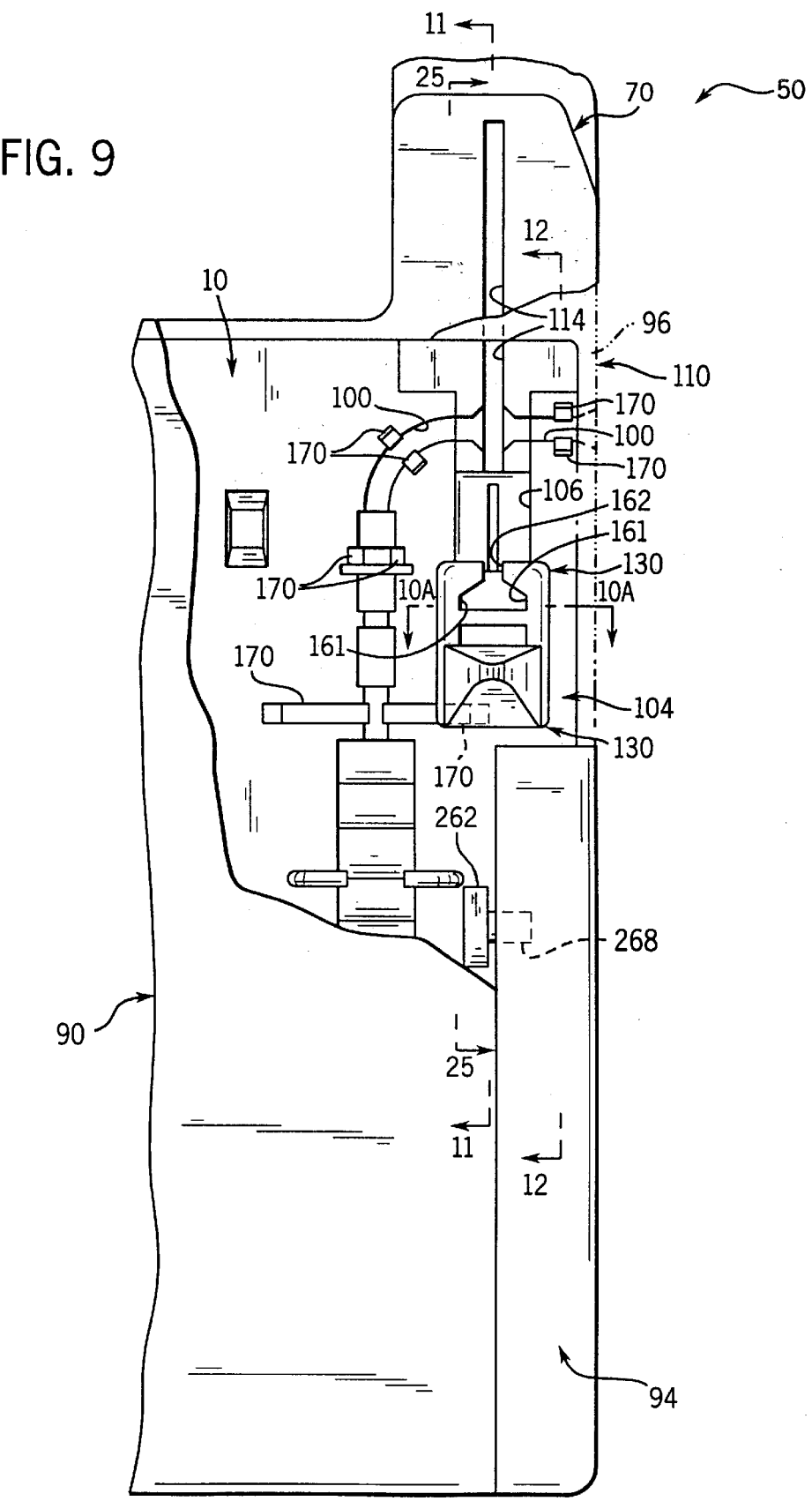
FIG. 9 is a fragmentary, front elevational view similar to FIG. 4, but FIG. 9 shows the door closed and partially broken away.

The door 90 is preferably mounted on a generally vertical axis for pivoting between the open and closed positions. In the preferred embodiment illustrated, the pivot axis of the door 90 is parallel to the portion of the tubing receiving path defined along the face of the pump head 174 and is also parallel to the direction of the movement of the carrier 130 between the elevated position (FIGS. 7, 7A, and 10C) and the lowered position (FIGS. 7B, 9 and 10B).

In particular, the door pivot axis is defined in the chassis 104, as shown in FIG. 28, by a pair of door pin-receiving projections 220. As illustrated in FIG. 7, the door 90 defines two slots 224 for each receiving one of the chassis projections 220. Each of the chassis projections 220 defines a pin-receiving bore 226, and the bores 226 are aligned with bores in the door 90, such as an upper bore 228 visible in FIG. 7. Pins, such as the upper pin 230 visible in FIG. 7, are disposed in the bores in the door 90 and chassis projections 220 for providing a connection accommodating pivoting movement of the door 90.

It will also be appreciated that when the slide clamp 60 is properly inserted in the pump carrier 130 as shown in FIG. 7, the clamp aperture 142 lies in a plane parallel to the door pivot axis.

It may also be noted that the inside of the door 90 includes an upper groove 240 (FIGS. 3 and 7) and a cavity or recess 242 (FIGS. 3 and 7) for receiving the outwardly projecting portions of the slide clamp 60 and carrier 130, respectively, when the door 90 is closed.

The door handle 94 includes a bore 244 as shown in FIG. 31 for receiving a pin 246 (FIGS. 7 and 12) pivotally mounting the handle 94 to the door 90 for rotation between the open position (FIG. 7) and the closed position (FIG. 2). The handle 94 includes an arcuate latch slot 250 (FIG. 31) and an exterior camming surface 254 (FIGS. 31 and 32).

As shown in FIGS. 7, 8A, 12, and 28, the housing chassis 104 defines a recessed latch region 260 for receiving the curved camming surface 254 of the door handle 94. Projecting outwardly from the edge of the chassis 104 adjacent the latch region 260 is a boss 262 (FIG. 7). In the preferred embodiment illustrated, the boss 262 is a separate metal insert which is mounted in a receiving cavity 264 (FIG. 28) in the chassis 104.

Figure 8A:
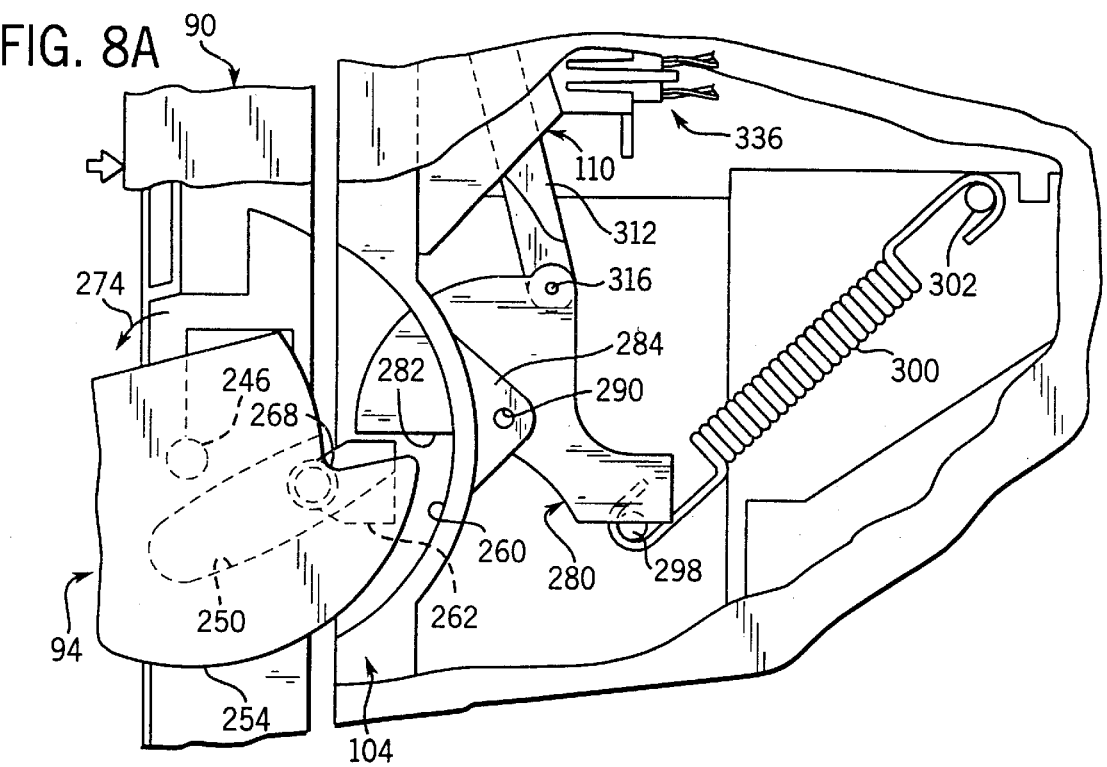
FIG. 8A is an enlarged, fragmentary, side elevational view of the pump with a portion of the pump housing broken away and showing the door latch area of the pump with the door closed and with the door handle in an open position but beginning to move toward the latch closed position.
Figure 8B:
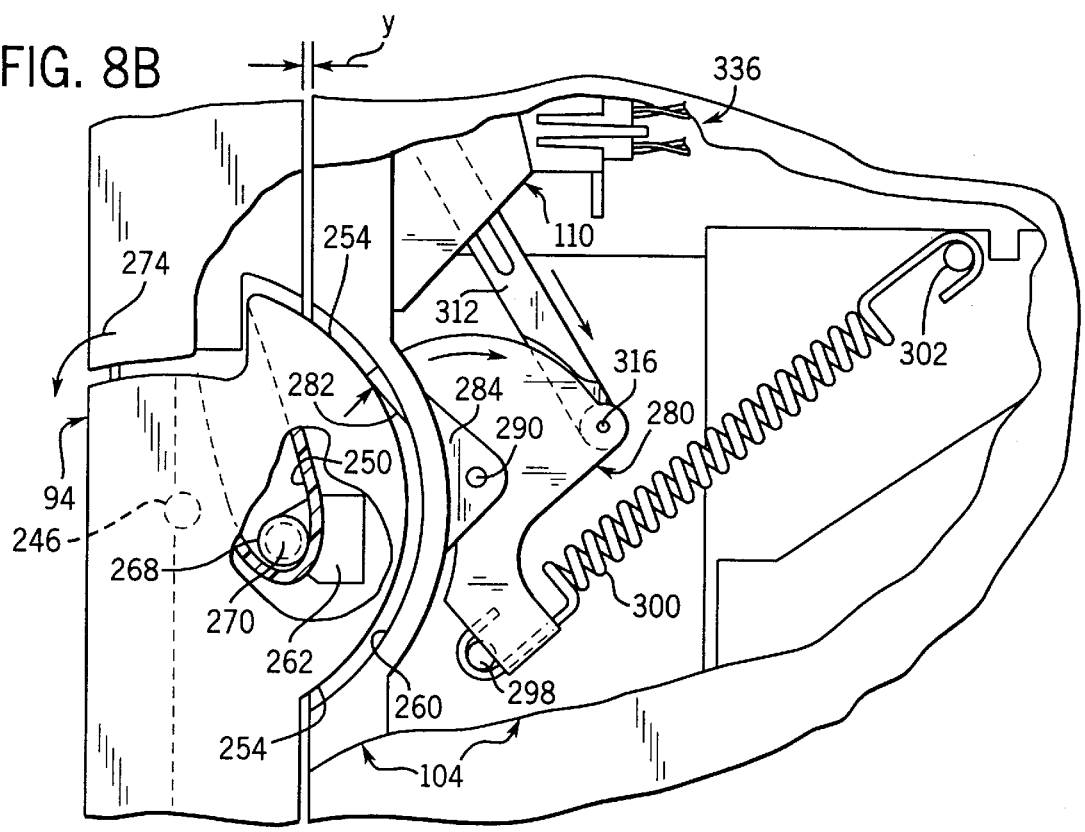
FIG. 8B is a view similar to FIG. 8A, but FIG. 8B shows the door handle in the fully latched closed position.
Figure 12:
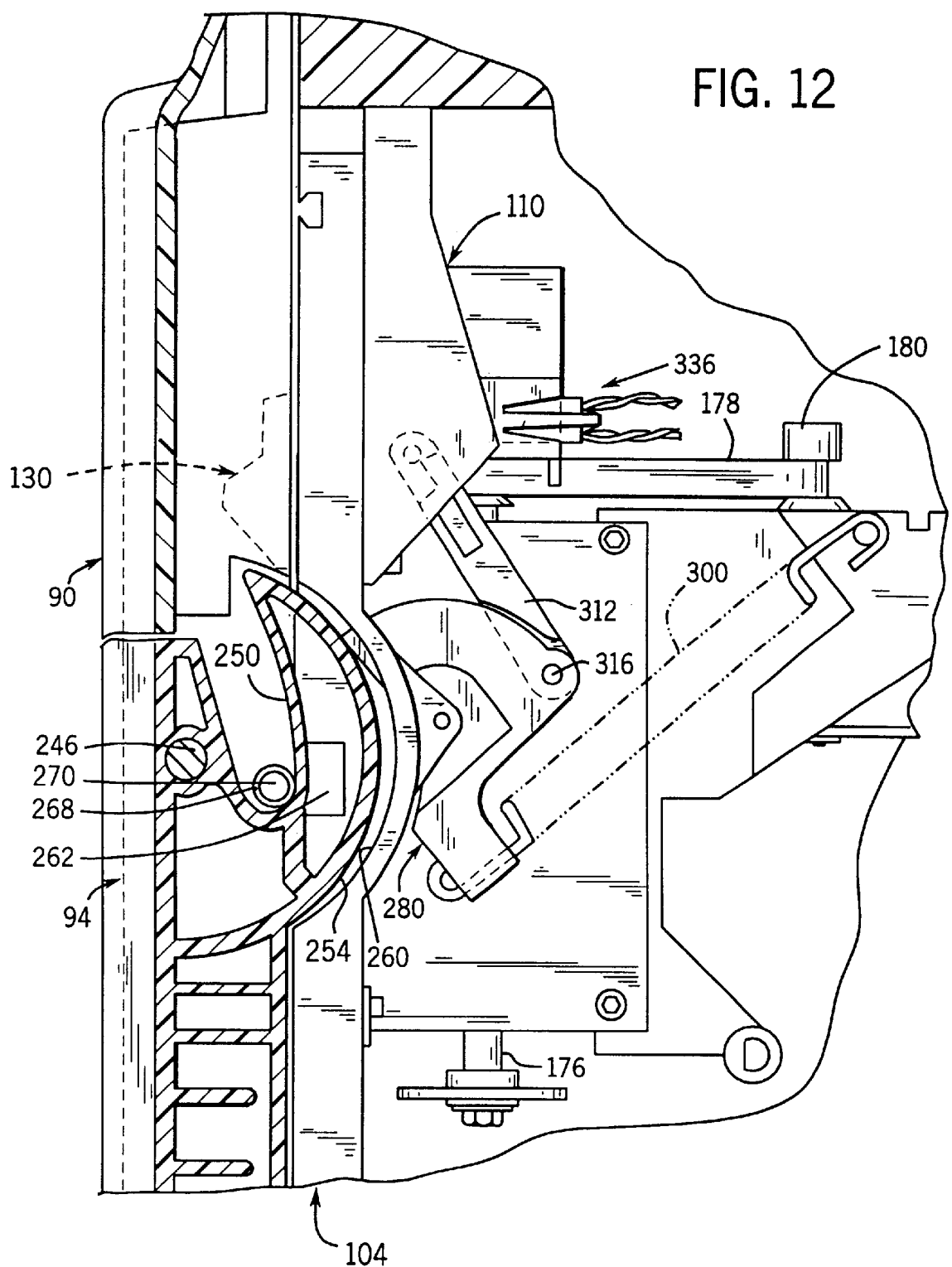
FIG. 12 is a enlarged, fragmentary, cross-sectional view taken generally along the plane 12—12 in FIG. 9.

As shown in FIG. 7, a latch roller 268 is disposed on a pin 270 mounted in the boss 262. When the door 90 is closed, the latch pin 270 and roller 268 are received in the arcuate slot 250 of the handle 94 as shown in FIG. 8A. As the handle 94 is rotated about the handle pivot pin 246 in the direction of the arrow 274 in FIG. 8A, the handle latch slot 250 slides along the roller 268 until the handle 94 is in the fully closed orientation as shown in FIGS. 8B, 11, and 12. Owing to (1) the curvature of the latch slot 250, and (2) the relative positions of the door handle pivot pin 246 and the latch pin roller 268, the resiliency of the system (especially as may be provided by the spring-biased platen 186 in the door 90) creates an over-center toggle latch action holding the door handle 94 in the fully closed position to maintain the door 90 latched closed.

Figure 19:
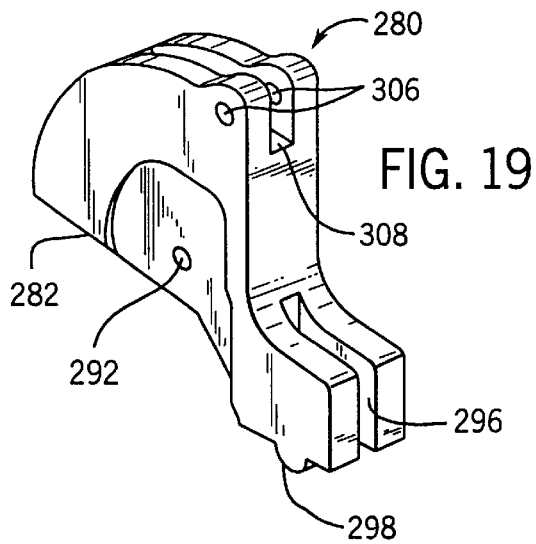
FIG. 19 is a perspective view of the crank, and the crank is shown removed from the pump in an orientation as it would appear if it were in the pump and viewed from the rear, upper, right-hand corner of the pump.
Figure 20:
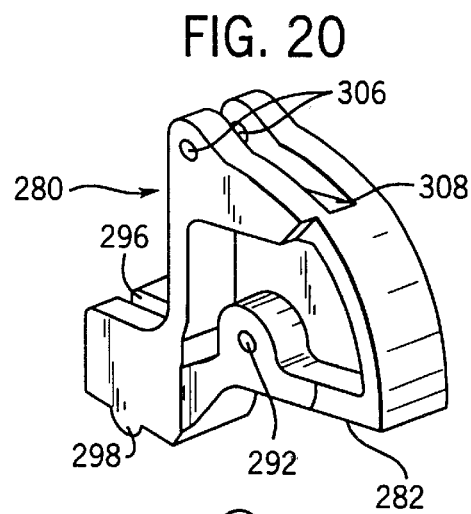
FIG. 20 is a perspective view of the opposite side of the crank shown in FIG. 19.

The carrier 130 (FIG. 7) has previously been described as being movable between an elevated position (FIGS. 7, 7A, and 10B) and a lowered position (FIGS. 7B, 9, and 10C). The movement of the door handle 94 to the closed, latched position (illustrated in FIGS. 2, 9, 8B, and 11), effects movement of the carrier 130 between the elevated and lowered positions by a novel linkage mechanism which is next described. In particular, the exterior camming surface 254 on the door handle 94 is designed to engage a cam follower element or crank 280 (FIGS. 7, 8B, 11, 19, and 20). The crank 280 defines a cam follower surface 282. As shown in FIG. 7, the portion of the crank 280 defining the cam follower surface 282 extends through a slot 283 in a portion of the chassis 104 which defines the recessed latch region 260. The crank 280 is pivotally mounted to the back of the chassis 104 adjacent the recessed latch region 260. As can be seen in FIG. 29, the chassis 104 has a pair of spaced-apart, rearwardly projecting, mounting bosses 284, and each boss 284 defines a bore 286 for receiving a pin 290 (FIGS. 8A and 8B). As illustrated in FIGS. 19 and 20, the crank 280 includes a bore 292 for receiving the pin 290 when the crank 280 is disposed between the chassis bosses 284 and pivotally mounted therein as shown in FIGS. 7, 8A, and 8B.

As shown in FIGS. 19 and 20, the crank 280 includes a slot 296 and a bridging rib 298. As shown in FIGS. 8A and 8B, one end of a helical coil tension spring 300 is engaged with the crank bridge 298, and the other end of the spring 300 is engaged with a pin 302 mounted in the side of the chassis 104. The spring 300 normally biases the crank 280 in a counterclockwise direction as viewed in FIGS. 8A and 8B so as to position the crank cam follower surface 282 in the recessed latch region 260 when the door handle 94 is in the unlatched or open orientation (FIG. 8A).

Figure 21:
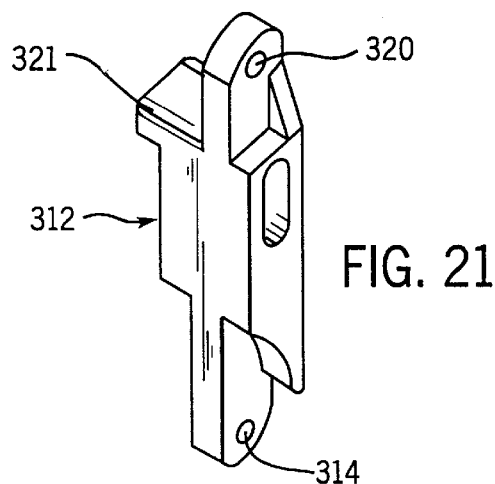
FIG. 21 is a perspective view of the connecting arm, and the arm is shown removed from the pump in an orientation as it would appear if it were in the pump and viewed from the front, upper right-hand corner of the pump.
Figure 22:
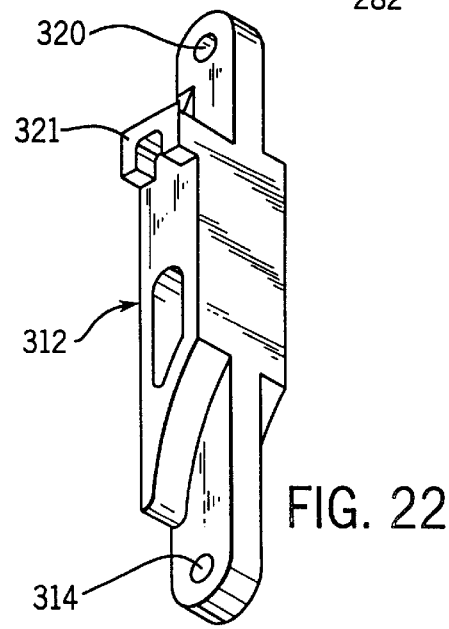
FIG. 22 is a perspective view of the connecting arm as viewed from below, left.

As shown in FIGS. 19 and 20, the crank 280 defines a bore 306 in a portion of the crank having a slot 308 which is adapted to receive one end of a link or arm 312 (FIGS. 7, 8A, and 11). As shown in FIGS. 21 and 22, the link or arm 312 has a reduced width lower end defining a bore 314. The reduced width lower end of the arm 312 is adapted to be received within the crank slot 308 and pivotally connected to the crank 280 by means of a pin 316 (FIGS. 8A, 8B, 11, and 12) which extends through the crank bore 306 and through the bore 314 of the link or arm 312.

The link or arm 312 extends upwardly into the open rear portion of the skirt 110. FIG. 26 shows that the bottom of the skirt 110 is open and that the interior of the skirt is generally hollow so as to accommodate the upper end of the arm 312 and other components, such as the rear portion 160 of the carrier 130 (as seen in FIG. 11). The upper end of the link 312 is connected to the rear portion 160 of the carrier 130 as shown in FIG. 11. Specifically, the upper end of the link or arm 312 defines a receiving bore 320 (FIGS. 21 and 22) for receiving a connecting pin 324 (FIGS. 11 and 25A).

Also, as can be seen in FIGS. 13, 14, 15, 17, and 18, the rear portion 160 of the carrier 130 defines a receiving bore 322 for the pin 324 and a receiving slot 323 for the upper end of the arm 312. The upper end of the arm 312 is retained within the slot 323 by means of the pin 324 (FIGS. 11 and 25A) which extends through the carrier bore 322 (FIGS. 15 and 25A) and the arm bore 320 (FIGS. 25A, 21, and 22).

An optional system for sensing the presence of the clamp 60 in the carrier may be incorporated in the pump, and such a system can include a rigid flag 328 (FIGS. 7A, 7B, 11, 23, 24, and 25). The carrier slot 155 (FIGS. 14, 15, and 17) receives a portion of the flag 328 extending therein as shown in FIGS. 7A, 7B, 11, and 25A. The flag 328 defines a bore 330 (FIGS. 23, 24, and 25A) for receiving the above-described pin 324 (FIG. 11) which pivotally connects the arm 312 to the rear portion 160 of the carrier 130.

Figure 23:
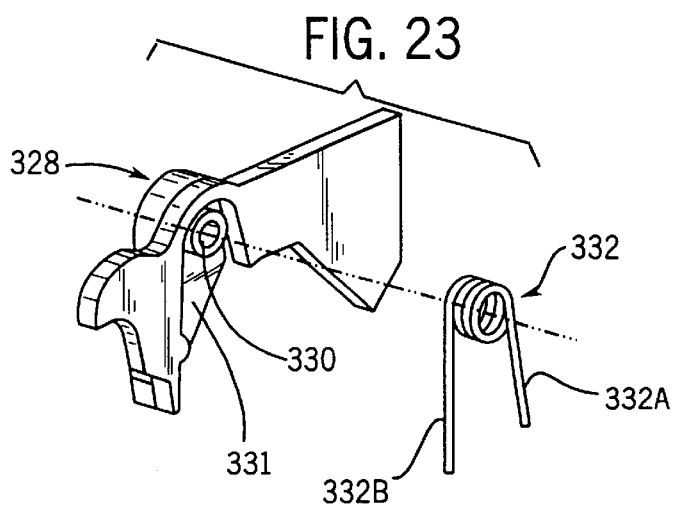
FIG. 23 is a perspective view of the slide clamp sensor flag, and the flag is shown removed from the pump in an orientation as it would appear if it were in the pump and viewed from the front, upper right-hand front corner of the pump.
Figure 24:
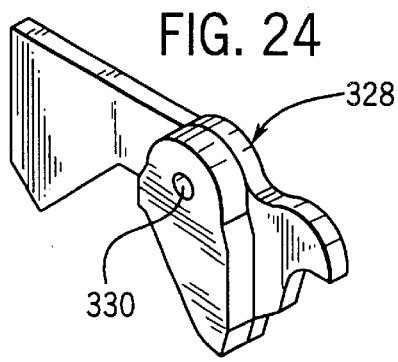
FIG. 24 is a perspective view of the flag as seen from the side opposite that shown in FIG. 23.

As shown in FIG. 23, the flag 328 defines a recess 331 for receiving a torsion spring 332 having a first leg 332A and a second leg 332B. As shown in FIG. 21, the upper portion of the link arm 312 defines a laterally extending shoulder 321. The shoulder 321 is engaged by the torsion spring leg 332A (FIG. 25). The other torsion spring leg 332B engages the front wall of the recess 331 in the flag 328 (FIGS. 23 and 25). The torsion spring 332 thus functions to bias the torsion spring so as to pivot the flag 328 about the pin 324 in a clockwise direction as viewed in FIGS. 7A, 7B, 11, and 12. This causes the front portion of the flag 328 to move upwardly into the bottom of the slot 161 of the carrier 130 whenever the slide clamp 60 is not present in the carrier 130. The clockwise rotation of the flag 328 into the carrier slots 155 and 161 is limited by the engagement of the lower front portion of the flag 328 with the carrier bridge 153 (FIG. 11). However, when the slide clamp 60 is inserted into the carrier (as shown in FIG. 7A), then the upper front edge of the flag 328 is engaged, and cammed downwardly, by the bottom of the clamp 60. This causes the flag 328 to pivot counterclockwise as viewed in FIG. 7A. The operation of the flag 328 in conjunction with a flag position sensor to control the pump 50 is described in detail hereinafter.

It will be appreciated that when the door 90 is open, the spring 300 pulls the crank 280 to pivot the crank 280 counterclockwise as viewed in FIGS. 7 and 7A. This holds the arm 312 and carrier 130 in the elevated position which accommodates insertion or removal of the slide clamp 60. On the other hand, when the door 90 is shut and the door handle 94 is latched closed as explained in detail above, the door handle camming surface 254 engages the cam follower surface 282 of the crank 280 and causes the crank 282 to pivot clockwise (as viewed in FIGS. 8B, 11, and 12). This pulls the carrier 130 (and slide clamp 60 disposed therein) to the lower position (FIGS. 7B, 8B, 11, and 12). Subsequently, when the door handle 94 is unlatched and lifted upwardly toward the position illustrated in FIG. 8A, the spring 300 again causes the crank 280 and arm 312 to return the carrier 130 (and slide clamp 60 carried therein) to the elevated position (FIGS. 7 and 7A).

When the carrier 130 is returned to the elevated position (FIG. 7), the slide clamp 60 can be removed. It will be appreciated that when the carrier 130 is in the elevated position, the slide clamp 60 is oriented on the tubing 54 in the receiving path such that the tubing 54 is squeezed closed in the narrow portion 144 of the clamp aperture 142 (FIG. 7A) as previously described. Hence, whenever the door 90 is opened to permit removal of the slide clamp 60, the tubing 54 is always squeezed closed by the slide clamp 60. Thus, if medical personnel fail to close the roller clamp 56 (FIG. 1) prior to removing the tubing 54 from the pump, then there will be no danger of fluid free flowing into the patient even if the lower clamp 190 is opened and the tubing 54 is removed from the pump.

An optional sensor system preferably includes a photoelectric sensor 336 which has a slot for accommodating movement of the rear portion of the flag 328 through the sensor 336. As shown in FIGS. 7A, 7B, and 11, the sensor 336 includes a conventional assembly 338 which includes a vertical slot with a light-emitting diode on one side of the slot and an aligned, light-receiving photoelectric cell on the other side of the slot. The rear portion of the flag 328 can pass through the slot.

The control system for the pump is designed to prevent operation of the pump whenever the power to the pump is turned on and the light path between the light-emitting diode and photoelectric cell in the assembly 338 is clear (i.e., not blocked by the flag 328). However, whenever the path in the light-emitting diode and photoelectric cell assembly 338 is blocked by the flag 328, the pump control system permits the pump to be operated.

As shown in FIG. 7A, if the slide clamp 60 is installed in the elevated carrier 130, but the pump door 90 is left open, then the flag 328 is above the sensor 336. The light-emitting diode and photoelectric cell assembly 338 is thus clear, and the unblocked sensor signal is processed by the control system to prevent operation of the pump because the door 90 is open.

If the slide clamp 160 is removed from the pump while the door is open (with the carrier 130 in the elevated position as shown in FIGS. 3 and 7A), then the torsion spring 332 will pivot the flag so that the rear portion of the flag 328 moves downwardly (to the dashed line position shown in FIG. 7A), but not far enough to block the light-emitting diode and photoelectric cell assembly 338. The unblocked sensor signal will thus still prevent the pump from operating.

If the door 90 is latched closed when the slide clamp 60 is not installed in the carrier 130, then the empty carrier 130 will be pulled to the lower position illustrated in FIG. 11. The torsion spring 332 will bias the flag 328 so that the rear portion of the flag 328 is below the light-emitting diode and photoelectric cell assembly 338 (as shown in FIG. 11).

Thus, the unblocked signal of the sensor 336 will still prevent operation of the pump in the condition wherein the pump door 90 is closed without the slide clamp 60 being installed.

However, if the slide clamp 60 is installed in the carrier 130 and the door 90 is latched closed to move the carrier 130 and clamp 60 down, then, as shown in FIG. 7B, the flag 328 is pivoted counterclockwise sufficiently by the clamp 60 so that the rear portion of the flag 328 moves upwardly to block the light-emitting diode and photoelectric cell assembly 338. The absence of a sensor signal is a permissive condition for the control system to allow operation of the pump.

The control system and sensor 336 may be provided with other operational modes, such as sensing the movement of the flag 338 between one position and another position for verifying movement sequences or other conditions. However, such other operational modes, as well as the basic sensor 336 and associated control system as described above, need not be included in the pump 50. Indeed, the incorporation of the flag 328 per se and flag sensor system in the pump 50 is an option that is not required.

It will be readily apparent from the foregoing detailed description of the invention and from the illustrations thereof that numerous variations and modifications may be effected without departing from the true spirit and scope of the novel concepts or principles of this invention.

What is claimed is:

1. A pump comprising:
   (a) a housing having a receiving path for receiving tubing through which fluid is pumped;
   (b) a door pivotable with respect to said housing about an axis; and
   (c) a carrier means on said housing for carrying a clamp on said tubing, said carrier means movable relative to said housing in a direction parallel to said axis; said carrier means includes a carrier defining first and second slots for receiving said clamp; and said second slot extends from, and is generally normal to, said first slot.

2. The pump in accordance with claim 1 in which
said door is pivotable about said axis between a closed position covering said receiving path and an open position exposing said receiving path; and
said carrier means includes a carrier adapted for holding said clamp on said tubing, and said clamp is an anti-free flow slide clamp.

3. The pump in accordance with claim 1 in which
said carrier means includes a carrier for holding said clamp in an orientation wherein a portion of said clamp projects beyond said carrier;
a portion of said receiving path adjacent said carrier includes a channel; and
said housing defines a groove that is (1) oriented generally normal to said channel, and (2) extends through said channel adjacent said carrier for receiving a portion of said clamp extending from said carrier.

4. A pump comprising:
a housing;
a receiving path defined along said housing for receiving tubing;
a door pivotable about an axis between a closed position covering said receiving path and an open position exposing said receiving path; and
a carrier on said housing for holding an anti-free flow slide clamp defining an elongate aperture, said carrier adapted to hold said clamp in an orientation wherein said clamp aperture lies in a plane parallel to said door axis.

5. The pump in accordance with claim 4 in which
said carrier is adapted to hold said clamp wherein said clamp has (1) a narrow portion for squeezing said tubing into a closed configuration, and (2) a wide portion for receiving said tubing in an unsqueezed, open configuration,
said carrier defines first and second slots for receiving said clamp; and
said second slot extends from, and is generally normal to, said first slot.

6. The pump in accordance with claim 4 in which
a portion of said receiving path adjacent said carrier includes a channel; and said housing defines a groove that is (1) oriented generally normal to said channel, and (2) extends through said channel adjacent said carrier for receiving a portion of said clamp extending from said carrier.

7. The pump in accordance with claim 4 in which said carrier is movable toward and away from a portion of said receiving path in opposite directions parallel to said door axis.

8. The pump in accordance with claim 4 in which said pump includes a pump head in said housing;

said pump is adapted to be disposed in a normal operating orientation wherein said pump has (1) a middle portion that includes said pump head, (2) an upper portion above said pump head, and (3) a lower portion below said pump head; and said receiving path is oriented substantially along a plane which is generally vertical when said pump is in said normal operating orientation.

9. The pump in accordance with claim 4 wherein the tubing is received in the elongate aperture.

10. A peristaltic pump comprising:

a housing;

a receiving path defined substantially in a plane along said housing for receiving tubing; and a carrier on said housing for holding an anti-free flow slide clamp, said carrier being moveable relative to said housing in a direction parallel to said plane defined by said receiving path, said clamp defines an elongate aperture having (1) a narrow portion for squeezing said tubing into a closed configuration, and (2) a wide portion for receiving said tubing in an unsqueezed, open configuration.

11. The pump in accordance with claim 10 in which said carrier defines first and second slots for receiving said clamp and said second slot extends from, and is generally normal to, said first slot.

12. The pump in accordance with claim 11 in which said carrier has a surface defining said second slot, and said surface has a detent for engaging said clamp.

13. The pump in accordance with claim 10 in which a portion of said receiving path adjacent said carrier includes a channel; and said housing defines a groove that is (1) oriented generally normal to said channel, and (2) extends through said channel adjacent said carrier for receiving a portion of said clamp that extends from said carrier.

14. The pump in accordance with claim 10 in which said pump has a door pivotable about an axis between a closed position covering said receiving path and an open position exposing said receiving path; and said carrier is movable toward and away from said receiving path in opposite directions parallel to said door axis.

15. The pump in accordance with claim 10 in which said pump includes a peristaltic pump head in said housing;

said pump is adapted to be disposed in a normal operating orientation wherein said pump has (1) a middle portion that includes said pump head, (2) an upper portion above said pump head, and (3) a lower portion below said pump head; and said receiving path is oriented substantially along a plane which is generally vertical when said pump is in said normal operating orientation.

16. A pump comprising:

a housing which defines (1) a receiving path for receiving tubing extending from an inlet end of said path to an outlet end of said path, and (2) a groove that is (a) oriented generally normal to a portion of said receiving path, and (b) communicates with said receiving path; and a carrier into which can be inserted an anti-free flow clamp, said carrier being located adjacent said housing receiving path and groove, said carrier defining first and second slots for receiving portions of said clamp, said second slot extending from said first slot, said second slot being generally normal to said first slot and aligned with said housing groove.

17. The pump in accordance with claim 16 in which a portion of said receiving path adjacent said carrier includes a channel which is generally normal to said groove.

18. The pump in accordance with claim 16 in which said carrier is movable toward and away from said receiving path in opposite directions parallel to said second slot and said groove.

19. The pump in accordance with claim 16 in which said pump includes a peristaltic pump head along said receiving path between said inlet end and said outlet end;

said pump is adapted to be disposed in a normal operating orientation wherein said pump has (1) a middle portion that includes said pump head, (2) an upper portion above said pump head, and (3) a lower portion below said pump head; and said receiving path is oriented substantially along a plane which is generally vertical when said pump is in said normal operating orientation.

20. The pump in accordance with claim 16 in which said pump includes a door having a closed position covering said receiving path and an open position exposing said receiving path.

21. In a pump which includes (1) a receiving path for receiving tubing extending from an inlet end of the path to an outlet end of the path, and (2) a peristaltic pump head along said receiving path between said inlet end and said outlet end, the improvement comprising:

a carrier into which can be inserted an anti-free flow clamp, said carrier being located adjacent said receiving path between said inlet end and said pump head; said carrier defines first and second slots for receiving said clamp; and said second slot extends from, and is generally normal to, said first slot.

22. The improvement in accordance with claim 21 in which said carrier is adapted to receive said clamp in the form of a unitary slide clamp which can be positioned on said tubing in a closed condition squeezing said tubing into a closed configuration;

said pump is adapted to be disposed in a normal operating orientation wherein said pump has (1) a middle portion that includes said pump head, (2) an upper portion above said pump head, and (3) a lower portion below said pump head;

said receiving path is oriented substantially along a plane which is generally vertical when said pump is in said normal operating orientation;

said inlet end is located in said upper portion; and said outlet end is located in said lower portion.

23. The improvement in accordance with claim 21 in which
said carrier is movable generally perpendicularly relative to at least a portion of said receiving path; and
said portion of said receiving path adjacent said carrier includes a channel.

24. The improvement in accordance with claim 23 in which said pump defines a groove that is (1) oriented generally normal to said channel, and (2) extends through said channel adjacent said carrier for receiving a portion of said clamp extending from said carrier.

25. In a pump which includes (1) a receiving tubing extending from an inlet end of the path to an outlet end of the path, and (2) a peristaltic pump head along said receiving path between said inlet end and said outlet end, the improvement comprising:
a carrier for holding an anti-free flow clamp on said tubing for operation between a closed condition squeezing said tubing into a closed configuration and an open condition in which said tubing is free to return to an open configuration, said barrier being lacated adjacent said receiving path between said inlet end and said pump head to position a portion of said clamp across said receiving path when said clamp is inserted into said carrier into said closed condition on said tubing so that said tubing can be loaded into said receiving path beginning at said inlet end and terminating at said outlet end; said pump has a door pivotable about an axis between a closed position covering said receiving path and an open position exposing said receiving path; and
said carrier is movable toward and away from said receiving path in opposite direction parallel to said door axis.

26. The improvement in accordance with claim 25 in which said carrier is movable toward and away from said adjacent receiving path.

27. The improvement in accordance with claim 25 in which
said carrier is adapted to receive said clamp in the form of a unitary slide clamp;
said pump is adapted to be disposed in a normal operating orientation wherein said pump has (1) a middle portion that includes said pump head, (2) an upper portion above said pump head, and (3) a lower portion below said pump head;
said receiving path is oriented substantially along a plane which is generally vertical when said pump is in said normal operating orientation;
said inlet end is located in said upper portion;
said outlet end is located in said lower portion;
a portion of said receiving path adjacent said carrier defines a channel; and
said pump defines a groove that (1) is oriented generally normal to said channel, and (2) extends through said channel adjacent said carrier for receiving a portion of said clamp extending from said carrier.

28. The pump in accordance with claim 25 in which
said pump is adapted to be disposed in a normal operating orientation wherein said pump has (1) a middle portion that includes said pump head, (2) an upper portion above said pump head, and (3) a lower portion below said pump head; and
said receiving path is oriented substantially along a plane which is generally vertical when said pump is in said normal operating orientation.

29. A pump comprising:
a housing;
a peristaltic pump head in said housing;
a receiving path defined along said housing and said pump head for receiving tubing;
a door pivotable about a first axis between a closed position covering said receiving path and an open position exposing said receiving path;
a carrier on said housing for holding an anti-free flow slide clamp defining an elongate aperture, said carrier adapted to hold said clamp in an orientation wherein said clamp aperture lies in a plane parallel to said door axis, said carrier being mounted on said housing to accommodate reciprocatable movement toward and away from a portion of said receiving path;
a handle pivotally mounted to said door about a second axis perpendicular to said first axis, said handle having a camming surface;
a cam follower element pivotally mounted to said housing about a third pivot axis for being engaged and pivoted by said handle camming surface when said handle is pivoted while said door is at said closed position;
a link pivotally connected to said cam follower element about a fourth pivot axis and pivotally connected to said carrier about a fifth pivot axis; and
a spring acting between said cam housing and said cam follower element to urge said follower element to pivot about said third pivot axis in a direction to move said carrier toward said portion of said receiving path.

30. A pump comprising:
(a) a housing having a receiving path that includes at least a portion lying in a straight line and that is adapted to receive tubing through which fluid is pumped; and
(b) a carrier means on said housing for carrying a clamp on said tubing, said carrier means movable relative to said housing in a direction parallel to said straight line; said carrier means includes a carrier adapted for holding an anti-free flow clamp defining an elongate aperture that lies generally in a plane and that has (1) a narrow portion for squeezing said tubing into a closed configuration, and (2) a wide portion for receiving said tubing in an unsqueezed, open configuration.

31. The pump in accordance with claim 30 in which said pump includes a peristaltic pump head lying along said receiving path straight line portion.

32. A system for delivering a fluid through tubing comprising:
(A) a clamp for clamping the tubing; and
(B) a pump including
(1) a housing having a receiving path for receiving the tubing through which the fluid is pumped; and
(2) a carrier mounted in said housing for carrying said clamp on the tubing, said carrier being movable relative to said housing, said carrier defines first and second slots for each receiving said clamp; and said second slot extends from, and is generally normal to, said first slot.

33. The system in accordance with claim 32 in which
said clamp has a laterally extending foot and a projecting portion extending from said foot, wherein said first and second slots receive said clamp foot and projecting portion, respectively.

34. The system in accordance with claim 32 in which
said carrier is adapted for holding said clamp in an orientation wherein a projecting portion of said clamp projects beyond said carrier;

a portion of said receiving path adjacent said carrier includes a channel; and said housing defines a groove that is (1) oriented generally normal to said channel, and (2) extends through said channel adjacent said carrier for receiving said projecting portion of said clamp extending from said carrier.

35. A pump comprising:

(a) a housing having a receiving path for receiving tubing though which fluid is pumped;

(b) a door pivotable with respect to said housing about an axis;

(c) a carrier on said housing for carrying a clamp on said tubing, said carrier means movable relative to said housing in a direction parallel to said axis, said door is pivotable about said axis between a closed position covering said receiving path and an open position exposing said receiving path, said carrier is adapted for holding said clamp on said tubing, and said clamp is an anti-free flow clamp having an elongate aperture for receiving the tubing.

* * * * *